United States Patent
DeFelippis et al.

(10) Patent No.: US 7,144,863 B2
(45) Date of Patent: Dec. 5, 2006

(54) GLP-1 FORMULATIONS WITH PROTRACTED TIME ACTION

(75) Inventors: Michael Rosario DeFelippis, Carmel, IN (US); Henry Acken Havel, Indianapolis, IN (US); Kenneth F. Mace, Fishers, IN (US); Kingman Ng, Carmel, IN (US); Virender Kumar Sarin, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 283 days.

(21) Appl. No.: 10/477,034

(22) PCT Filed: May 21, 2002

(86) PCT No.: PCT/US02/15137

§ 371 (c)(1),
(2), (4) Date: Nov. 6, 2003

(87) PCT Pub. No.: WO02/098348

PCT Pub. Date: Dec. 12, 2002

(65) Prior Publication Data

US 2005/0043228 A1      Feb. 24, 2005

Related U.S. Application Data

(60) Provisional application No. 60/295,282, filed on Jun. 1, 2001.

(51) Int. Cl.
*A61K 38/16* (2006.01)
*A61K 38/26* (2006.01)

(52) U.S. Cl. ......................................... 514/14; 530/308

(58) Field of Classification Search .................... None
See application file for complete search history.

(56) References Cited

U.S. PATENT DOCUMENTS 6,720,407 B1 *   4/2004   Hughes et al. ............... 530/324

FOREIGN PATENT DOCUMENTS

EP      0 619 322      10/1994

OTHER PUBLICATIONS

Kim, et al., "Precipitation of Insulinotropin in the Presence of Protamine:Effect of Phenol and Zinc on the Isophane Ratio and the Insulinotropin Concentration in the Supernatant." Pharmaceutical Research, 1995, vol. 12, No. 9, pp. 1284-1288.
Pridal, L. et al., "Absorption of Glucagon-Like Peptide-1 Can Be Protracted By Zinc or Protamine." International Journal of Pharmaceutics, 1996, vol. 136; pp. 53-59.

* cited by examiner

*Primary Examiner*—Anish Gupta
(74) *Attorney, Agent, or Firm*—Gregory A. Cox; Alejandro Martinez

(57) ABSTRACT

The present invention encompasses compositions wherein a GLP-1 compound is complexed with a basic polypeptide. The compositions provide a prolonged duration of action and can be administered by the pulmonary route.

18 Claims, No Drawings

GLP-1 FORMULATIONS WITH PROTRACTED TIME ACTION

This is the national phase application, under 35 USC 371, for PCT/US02/15137, filed May 21, 2002, which claims the priority of U.S. provisional application No. 60/295,282, filed Jun. 1, 2001.

FIELD OF THE INVENTION

This invention is in the field of human medicine. In particular, this invention is in the field of long-acting glucagon-like peptide-1 (GLP-1) particles useful in the treatment of diseases such as type 2 diabetes.

BACKGROUND OF THE INVENTION

Over the past several decades, continuous strides have been made to improve the treatment of diabetes mellitus. Approximately 90% of people with diabetes have type 2 diabetes also known as non-insulin dependent diabetes mellitus (NIDDM). Type 2 diabetics generally still make insulin, but the insulin cannot be used effectively by the body's cells. This is primarily because the amount of insulin produced in response to rising blood sugar levels is not sufficient to allow cells to efficiently take up glucose and thus, reduce blood sugar levels.

Often, individuals with NIDDM can initially control their blood glucose levels by taking oral medications. However, oral medications do not slow the progressive loss of β cell function that occurs in type 2 patients and eventually these types of medications are not sufficient to control blood glucose levels.

A large body of pre-clinical and clinical research data suggests that glucagon-like pepide-1 (GLP-1) shows great promise as a treatment for NIDDM especially when oral agents begin to fail. GLP-1 induces numerous biological effects such as stimulating insulin secretion, inhibiting glucagon secretion, inhibiting gastric emptying, enhancing glucose utilization, and inducing weight loss. Further, pre-clinical studies suggest that GLP-1 may also act to prevent the β cell deterioration that occurs as the disease progresses. Perhaps the most salient characteristic of GLP-1 is its ability to stimulate insulin secretion without the associated risk of hypoglycemia that is seen when using insulin therapy or some types of oral therapies that act by increasing insulin expression.

As NIDDM progresses it becomes extremely important to achieve near normal glycemic control and thereby minimize the complications associated with prolonged hyperglycemia. GLP-1 would appear to be the drug of choice. However, the usefulness of therapy involving GLP-1 peptides has been limited by the fact that GLP-1(1–37) is poorly active, and the two naturally occurring truncated peptides, GLP-1(7–37) OH and GLP-1(7–36)$NH_2$, are rapidly cleared in vivo and have extremely short in vivo half-lives. Further, current GLP-1 peptide formulations cannot be given orally and like insulin must be injected. Thus, despite the clear medical advantages associated with therapy involving GLP-1, the short half-life which results in a drug that must be injected numerous times a day has impeded commercial development efforts.

Generally, moving patients to an injectable therapy is quite difficult. Many diabetics are unwilling to undertake any type of intensive injection therapy due to the discomfort associated with the many injections required to maintain adequate glucose control. Furthermore, diabetics on insulin are generally required to monitor their blood glucose which involves additional needle sticks. This type of therapy can be both physchologically and physically painful. This is especially true when patients have been treated solely with oral medications throughout the progression of the disease.

Thus, not only is there a need to develop GLP-1 formulations that provide a protracted action when injected such that the number of injections is reduced and glucose monitoring is eliminated, but also GLP-1 formulations that can be delivered by alternative means such as by the pulmonary route and provide a sustained pharmacokinetic profile.

It has been known for a number of years that some proteins can be absorbed through the lung; however, despite this showing, pulmonary delivery has not received wide acceptance as a means for delivering therapeutic peptides. This is due to dramatic decreases in bioavailability that can occur when a peptide is delivered as well as extreme variability in amounts of a particular peptide absorbed even when comparing identical doses given at different times. Efficient pulmonary delivery of a peptide is dependent on the ability to deliver the peptide to the deep lung alveolar epithelium. The extent to which peptides are eliminated before reaching the deep lung depends on characteristics such as size and aerodynamic properties of particles containing the peptide.

By complexing GLP-1 molecules with a basic polypeptide such as protamine and incorporating these complexes into unique particles, the present invention solves the problems associated with the rapid clearance and short half-life of GLP-1 compounds as well as the inefficiency and reduced bioavailability that can occur when peptides are delivered through the pulmonary route. Furthermore, the GLP-1 particles of the present invention have sustained release properties when delivered pulmonarily.

It is known in the art that native GLP-1(7–37)OH can be precipitated with protamine. EP 619322 describes aqueous suspensions of native GLP-1 and protamine which the inventors suggest have a protracted action when administered subcutaneously. In addition, Pridal, et al. discusses protamine-GLP-1 crystals and state that the protracted action of these crystals is due to their slow absorption rate from the subcutaneous injection site. Pridal, et al. (1996) *Intln. J. Pharm.* 136:53–59. However, the authors use a ratio of GLP-1 to protamine such that the resulting crystals are of a size not particularly suited for efficient pulmonary delivery. Kim et al. also discusses precipitation of native GLP-1 and protamine. Kim, et al. (1995) *Pharm. Res.* 12:1284–1288. That paper focuses solely on determining the isophane ratio of native GLP-1 to protamine in the presence of various excipients.

This GLP-1 protamine art, however, does not describe the unique particles and compositions encompassed by the present invention. These particles and compositions have properties such as size, solubility characteristics, morphology, and mass mean aerodynamic diameters as well as other aerodynamic properties that distinguish them from the prior art precipitated mixtures. Furthermore, none of the prior art references disclose or suggest the dry powder formulations of the present invention which comprise a mixture of unique particles containing GLP-1, GLP-1 analogs, or GLP-1 derivatives complexed with a basic polypeptide such as protamine. These particles are sufficiently small and possess aerodynamic properties such that they reach the deep lung thereby reducing problems associated with bioavailability and absorption variability. Most importantly, the particles of the present invention and formulations thereof have a sustained pharmacokinetic profile when delivered pulmonarily.

SUMMARY OF THE INVENTION

In one form thereof, the present invention provides a composition comprising particles wherein the particles are comprised of a GLP-1 compound complexed with a basic polypeptide. The basic polypeptide is selected from the group consisting of polylysine, polyarginine, polyornithine, protamine, putrescine, spermine, spermidine, and histone. The mass ratio of GLP-1 compound to basic polypeptide in the composition is between about 4:1 and about 10:1. The mean number diameter of the particles is between 1 μm and 5 μm.

Preferably, the GLP-1 compound comprises a peptide of formula III (SEQ ID NO:3)

```
 7   8   9  10  11  12  13  14  15  16  17
Xaa-Xaa-Xaa-Gly-Xaa-Xaa-Thr-Xaa-Asp-Xaa-Xaa- 18  19  20  21  22  23  24  25  26  27  28
Xaa-Xaa-Xaa-Xaa-Xaa-Xaa-Xaa-Xaa-Xaa-Xaa-Phe- 29  30  31  32  33  34  35  36  37  38  39
Ile-Xaa-Xaa-Xaa-Xaa-Xaa-Xaa-Xaa-Xaa-Xaa-Xaa- 40  41  42  43  44  45
Xaa-Xaa-Xaa-Xaa-Xaa-Xaa
``` wherein:
Xaa at position 7 is: L-histidine, D-histidine, desamino-histidine, 2-amino-histidine, β-hydroxy-histidine, homohistidine, α-fluoromethyl-histidine or α-methyl-histidine;
Xaa at position 8 is Ala, Gly, Ser, Thr, Leu, Ile, Val, Glu, Asp, or Lys;
Xaa at position 9 is Glu, Asp, Lys, Thr, Ser, Arg, Trp, Phe, Tyr, or His;
Xaa at position 11 is Thr, Ala, Gly, Ser, Leu, Ile, Val, Glu, Asp, Arg, His, or Lys;
Xaa at position 14 is Ser, Ala, Gly, Thr, Leu, Ile, Val, Glu, Asp, or Lys;
Xaa at position 12 is His, Trp, Phe, or Tyr
Xaa at position 16 is Val, Ala, Gly, Ser, Thr, Leu, Ile, Tyr, Glu, Asp, Trp, His, Phe, or Lys;
Xaa at position 17 is Ser, Ala, Gly, Thr, Leu, Ile, Val, Glu, Asp, or Lys;
Xaa at position 18 is Ser, Ala, Gly, Thr, Leu, Ile, Val, Glu, Asp, His, Pro, Arg, or Lys;
Xaa at position 19 is Tyr, Phe, Trp, Glu, Asp, Gly, Gln, Asn, Arg, Cys, or Lys;
Xaa at position 20 is Leu, Ala, Gly, Ser, Thr, Ile, Val, Glu, Asp, Met, or Lys;
Xaa at position 21 is Glu, Asp, or Lys;
Xaa at position 22 is Gly, Ala, Ser, Thr, Leu, Ile, Val, Glu, Asp, or Lys;
Xaa at position 23 is Gln, Asn, Arg, Glu, Asp, His, or Lys;
Xaa at position 24 is Ala, Gly, Ser, Thr, Leu, Ile, Val, Arg, Glu, Asp, or Lys;
Xaa at position 25 is Ala, Gly, Ser, Thr, Leu, Ile, Val, Glu, Asp, or Lys;
Xaa at position 26 is Lys, Arg, Gln, Glu, Asp, Trp, Tyr, Phe, or His;
Xaa at position 27 is Glu, Asp, Ala, His, Phe, Tyr, Trp, Arg, Leu, or Lys;
Xaa at position 30 is Ala, Gly, Ser, Thr, Leu, Ile, Val, Glu, Asp, His, or Lys;
Xaa at position 31 is Trp, Phe, Tyr, Glu, Asp, Ser, Thr, Arg, or Lys;
Xaa at position 32 is Leu, Gly, Ala, Ser, Thr, Ile, Val, Glu, Asp, or Lys;
Xaa at position 33 is Val, Gly, Ala, Ser, Thr, Leu, Ile, Glu, Asp, Arg, or Lys;
Xaa at position 34 is Lys, Arg, Glu, Asp, Asn, or His;
Xaa at position 35 is Gly, Ala, Ser, Thr, Leu, Ile, Val, Glu, Asp, Arg, Trp, Tyr, Phe, Pro, His, or Lys;
Xaa at position 36 is Arg, Lys, Glu, Asp, Thr, Ser, Trp, Tyr, Phe, Gly, or His;
Xaa at position 37 is Gly, Ala, Ser, Thr, Leu, Ile, Val, Glu, Asp, His, Lys, Arg, Trp, Tyr, Phe, Gly-Pro, Gly-Pro-NH$_2$, —NH$_2$ or is deleted;
Xaa at position 38 is Arg, Lys, Glu, Asp, Ser, or His, or is deleted;
Xaa at position 39 is Arg, Lys, Glu, Asp, Ser, or His, or is deleted;
Xaa at position 40 is Asp, Glu, Gly, or Lys, or is deleted;
Xaa at position 41 is Phe, Trp, Tyr, Glu, Asp, Ala, or Lys, or is deleted;
Xaa at position 42 is Pro, Lys, Glu, or Asp, or is deleted;
Xaa at position 43 is Glu, Asp, Pro, or Lys, or is deleted;
Xaa at position 44 is Glu, Asp, Pro, or Lys, or is deleted; and
Xaa at position 45 is Val, Glu, Asp, Ser, or Lys, or is deleted, or a C-1–6-ester, or amide, or C-1–6-alkylamide, or C-1–6-dialkylamide thereof; provided that when the amino acid at position 37, 38, 39, 40, 41, 42, 43, or 44 is deleted, then each amino acid downstream of that amino acid is also deleted;

and provided that no more than six amino acids differ from the corresponding amino acid in GLP-1(7–37)OH, Exendin 3, or Exendin 4.

Preferably, the basic polypeptide is selected from the group consisting of polyarginine, protamine, and polylysine. Most preferably, the basic polypeptide is protamine.

Preferably the ratio of GLP-1 compound to basic polypeptide in the composition is between about 5:1 and about 10:1. More preferably the ratio of GLP-1 compound to basic polypeptide in the composition is between about 6:1 and about 10:1. Most preferably the ratio of GLP-1 compound to basic polypeptide in the composition is between about 7:1 and about 9:1.

Preferably, the number mean diameter of the particles is between 3 μm and 5 μm, with 90% of the particles in the composition being less than 12 μm. Preferably, 90% of the particles being less than 9 μm, more preferably, less than 7 μm.

The composition of particles may further comprise a divalent metal ion, such as zinc at a molar ratio of less than about 2:1 (Zinc:GLP-1 compound).

The composition of particles may be a suspension, a solution, or a dry powder. Preferably, the composition is spray dried. The dried powder has an aerodynamic particle size of about 3 μm to about 5 μm, and true density of between about 1.25 g/cc and 1.45 g/cc.

The present invention further provides a process of making the composition by preparing a GLP-1 solution comprised of a GLP-1 compound, preparing a basic polypeptide solution comprised of a basic polypeptide selected from the group consisting of polylysine, polyarginine, polyornithine, polyaspartic acid, polyglutamic acid, protamine, putrescine, spermine, spermidine, and histone, and adding an alcohol selected from the group consisting of ethanol, propanol, isopropanol, methanol, or mixtures thereof to either or both the GLP-1 solution and the basic polypeptide solution. The GLP-1 solution is mixed with the basic polypeptide solution. Optionally, zinc may be added to the mixture of the composition.

The present invention further provides a method of administering an effective amount of a composition comprising a GLP-1 compound complexed with a basic polypeptide to a patient by pulmonary means. The composition can be delivered from an inhalation device, such as a nebulizer, a metered-dose inhaler, a dry powder inhaler, and a sprayer. Preferably, the device is a dry powder inhaler.

The present invention further provides a method of treating diabetes, hyperglycemia, obesity, irritable bowel syndrome, myocardial infarction, or stroke using the compositions discussed herein.

The present invention further provides use of the composition for the preparation of a medicament in the treatment of diabetes, hyperglycemia, obesity, irritable bowel syndrome, myocardial infarction, and stroke in a mammal.

DETAILED DESCRIPTION OF THE INVENTION

The three-letter abbreviation code for amino acids used in this specification conforms with the list contained in Table 3 of Annex C, Appendix 2 of the PCT Administrative Instructions and with 37 CFR § 1.822(d)(1)(2000).

The GLP-1 peptides of the present invention can be made by a variety of methods known in the art such as solid-phase synthetic chemistry, purification of GLP-1 molecules from natural sources, recombinant DNA technology, or a combination of these methods. For example, methods for preparing GLP-1 peptides are described in U.S. Pat. Nos. 5,118,666, 5,120,712, 5,512,549, 5,977,071, and 6,191,102.

The particles and compositions thereof encompassed by the present invention include complexes containing GLP-1 compounds. The term "GLP-1 compounds" refers to the two naturally occurring truncated GLP-1 peptides, GLP-1(7–37)OH and GLP-1(7–36)NH$_2$, Exendin-3, Exendin-4, analogs thereof, and derivatives thereof. As is the custom in the art, the N-terminal residue of a GLP-1 compound is represented as position 7.

The two naturally occurring truncated GLP-1 peptides are represented in formula I (SEQ ID NO:1):

```
                                            SEQ ID NO: 1
7    8   9   10  11  12  13  14  15  16  17

His-Ala-Glu-Gly-Thr-Phe-Thr-Ser-Asp-Val-Ser- 18  19  20  21  22  23  24  25  26  27  28

Ser-Tyr-Leu-Glu-Gly-Gln-Ala-Ala-Lys-Glu-Phe- 29  30  31  32  33  34  35  36  37

Ile-Ala-Trp-Leu-Val-Lys-Gly-Arg-Xaa
``` wherein:
Xaa at position 37 is Gly, or —NH$_2$.

The GLP-1 compounds encompassed by the present invention have sufficient homology to GLP-1(7–37)OH or a fragment of GLP-1(7–37)OH such that the compound has the ability to bind to the GLP-1 receptor and initiate a signal transduction pathway resulting in stimulation of insulin secretion by the β-cells of the pancreas (insulinotropic action). Preferably, a GLP-1 compound has the amino acid sequence of SEQ ID NO.1 or is modified so that from one, two, three, four or five amino acids differ from SEQ ID NO:1.

Some GLP-1 compounds known in the art include, for example, GLP-1(7–34) and GLP-1(7–35), GLP-1(7–36), Gln$^9$-GLP-1(7–37), D-Gln$^9$-GLP-1(7–37), Thr$^{16}$-Lys$^{18}$-GLP-1(7–37), and Lys$^{18}$-GLP-1(7–37). GLP-1 compounds such as GLP-1(7–34) and GLP-1(7–35) are disclosed in U.S. Pat. No. 5,118,666, herein incorporated by reference. Other known biologically active GLP-1 analogs are disclosed in U.S. Pat. No. 5,977,071, herein incorporated by reference; U.S. Pat. No. 5,545,618, herein incorporated by reference; U.S. Pat. No. 5,705,483, herein incorporated by reference; U.S. Pat. No. 5,977,071, herein incorporated by reference; U.S. Pat. No. 6,133,235, herein incorporated by reference and Adelhorst, et al., *J. Biol. Chem.* 269:6275 (1994), herein incorporated by reference.

GLP-1 compounds also include polypeptides in which one or more amino acids have been added to the N-terminus and/or C-terminus of GLP-1(7–37)OH, or fragments or analogs thereof. Preferably from one to six amino acids are added to the N-terminus and/or from one to eight amino acids are added to the C-terminus of GLP-1(7–37)OH. It is preferred that GLP-1 compounds of this type have up to about thirty-nine amino acids. The amino acids in the "extended" GLP-1 compounds are denoted by the same number as the corresponding amino acid in GLP-1(7–37)OH. For example, the N-terminal amino acid of a GLP-1 compound obtained by adding two amino acids to the N-terminus of GLP-1(7–37)OH is at position 5; and the C-terminal amino acid of a GLP-1 compound obtained by adding one amino acid to the C-terminus of GLP-1(7–37)OH is at position 39. Amino acids 1–6 of an extended GLP-1 compound are preferably the same as or a conservative substitution of the amino acid at the corresponding position of GLP-1(1–37)OH. Amino acids 38–45 of an extended GLP-1 compound are preferably the same as or a conservative substitution of the amino acid at the corresponding position of Exendin-3 or Exendin-4. The amino acid sequence of Exendin-3 and Exendin-4 are represented in formula II (SEQ ID NO:2):

```
                                            SEQ ID NO: 2
7    8   9   10  11  12  13  14  15  16  17

His-Xaa-Xaa-Gly-Thr-Phe-Thr-Ser-Asp-Leu-Ser- 18  19  20  21  22  23  24  25  26  27  28

Lys-Gln-Met-Glu-Glu-Glu-Ala-Val-Arg-Leu-Phe- 29  30  31  32  33  34  35  36  37  38  39

Ile-Glu-Trp-Leu-Lys-Asn-Gly-Gly-Pro-Ser-Ser- 40  41  42  43  44  45

Gly-Ala-Pro-Pro-Pro-Ser
``` wherein:
Xaa at position 8 is Ser or Gly; and
Xaa at position 9 is Asp or Glu.

For the purposes of the present invention, a conservative substitution is the replacement of an amino acid with another amino acid that has the same net electronic charge and approximately the same size and shape. Amino acids with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acids with phenyl or substituted phenyl groups in their side chains are considered to have about the same size and shape.

A preferred group of GLP-1 compounds is comprised of GLP-1 analogs of formula III (SEQ ID NO:3):

```
7    8    9    10   11   12   13   14   15   16   17     SEQ ID
Xaa-Xaa-Xaa-Gly-Xaa-Xaa-Thr-Xaa-Asp-Xaa-Xaa-           NO: 3

18   19   20   21   22   23   24   25   26   27   28
Xaa-Xaa-Xaa-Xaa-Xaa-Xaa-Xaa-Xaa-Xaa-Xaa-Phe- 29   30   31   32   33   34   35   36   37   38   39
Ile-Xaa-Xaa-Xaa-Xaa-Xaa-Xaa-Xaa-Xaa-Xaa-Xaa- 40   41   42   43   44   45
Xaa-Xaa-Xaa-Xaa-Xaa-Xaa
``` wherein:

Xaa at position 7 is: L-histidine, D-histidine, desamino-histidine, 2-amino-histidine, β-hydroxy-histidine, homo-histidine, α-fluoromethyl-histidine or α-methyl-histidine;

Xaa at position 8 is Ala, Gly, Ser, Thr, Leu, Ile, Val, Glu, Asp, or Lys;

Xaa at position 9 is Glu, Asp, Lys, Thr, Ser, Arg, Trp, Phe, Tyr, or His;

Xaa at position 11 is Thr, Ala, Gly, Ser, Leu, Ile, Val, Glu, Asp, Arg, His, or Lys;

Xaa at position 14 is Ser, Ala, Gly, Thr, Leu, Ile, Val, Glu, Asp, or Lys;

Xaa at position 12 is His, Trp, Phe; or Tyr

Xaa at position 16 is Val, Ala, Gly, Ser, Thr, Leu, Ile, Tyr, Glu, Asp, Trp, His, Phe, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, His, Pro, Arg, or Lys;

Xaa at position 19 is Tyr, Phe, Trp, Glu, Asp, Gly, Gln, Asn, Arg, Cys, or Lys;

Xaa at position 20 is Leu, Ala, Gly, Ser, Thr, Ile, Val, Glu, Asp, Met, or Lys;

Xaa at position 21 is Glu, Asp, or Lys;

Xaa at position 22 is Gly, Ala, Ser, Thr, Leu, Ile, Val, Glu, Asp, or Lys;

Xaa at position 23 is Gln, Asn, Arg, Glu, Asp, His, or Lys;

Xaa at position 24 is Ala, Gly, Ser, Thr, Leu, Ile, Val, Arg, Glu, Asp, or Lys;

Xaa at position 25 is Ala, Gly, Ser, Thr, Leu, Ile, Val, Glu, Asp, or Lys;

Xaa at position 26 is Lys, Arg, Gln, Glu, Asp, Trp, Tyr, Phe, or His;

Xaa at position 27 is Glu, Asp, Ala, His, Phe, Tyr, Trp, Arg, Leu, or Lys;

Xaa at position 30 is Ala, Gly, Ser, Thr, Leu, Ile, Val, Glu, Asp, His, or Lys;

Xaa at position 31 is Trp, Phe, Tyr, Glu, Asp, Ser, Thr, Arg, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, Arg, or Lys;

Xaa at position 34 is Lys, Arg, Glu, Asp, Asn, or His;

Xaa at position 35 is Gly, Ala, Ser, Thr, Leu, Ile, Val, Glu, Asp, Arg, Trp, Tyr, Phe, Pro, His, or Lys;

Xaa at position 36 is Arg, Lys, Glu, Asp, Thr, Ser, Trp, Tyr, Phe, Gly, or His;

Xaa at position 37 is Gly, Ala, Ser, Thr, Leu, Ile, Val, Glu, Asp, His, Lys, Arg, Trp, Tyr, Phe, Gly-Pro, Gly-Pro-NH$_2$, —NH$_2$ or is deleted;

Xaa at position 38 is Arg, Lys, Glu, Asp, Ser, or His, or is deleted;

Xaa at position 39 is Arg, Lys, Glu, Asp, Ser, or His, or is deleted;

Xaa at position 40 is Asp, Glu, Gly, or Lys, or is deleted;

Xaa at position 41 is Phe, Trp, Tyr, Glu, Asp, Ala, or Lys, or is deleted;

Xaa at position 42 is Pro, Lys, Glu, or Asp, or is deleted;

Xaa at position 43 is Glu, Asp, Pro, or Lys, or is deleted;

Xaa at position 44 is Glu, Asp, Pro, or Lys, or is deleted, and

Xaa at position 45 is Val, Glu, Asp, Ser, or Lys, or is deleted, or a C-1–6-ester, or amide, or C-1–6-alkylamide, or C-1–6-dialkylamide thereof; provided that when the amino acid at position 37, 38, 39, 40, 41, 42, 43, or 44 is deleted, then each amino acid downstream of that amino acid is also deleted.

Another preferred group of GLP-1 compounds is comprised of GLP-1 analogs of formula IV (SEQ ID NO:4):

```
7    8    9    10   11   12   13   14   15   16   17
His-Xaa-Glu-Gly-Xaa-Xaa-Thr-Ser-Asp-Xaa-Ser- 18   19   20   21   22   23   24   25   26   27   28
Ser-Tyr-Leu-Glu-Xaa-Xaa-Xaa-Ala-Xaa-Xaa-Phe- 29   30   31   32   33   34   35   36   37
Ile-Ala-Xaa-Leu-Xaa-Xaa-Xaa-Xaa-R
``` wherein:

Xaa at position 8 is Gly, Ala, Val, Leu, Ile, Ser, or Thr;

Xaa at position 11 is Asp, Glu, Arg, Thr, Ala, Lys, or His;

Xaa at position 12 is His, Trp, Phe, or Tyr;

Xaa at position 16 is Leu, Ser, Thr, Trp, His, Phe, Asp, Val, Glu, or Ala;

Xaa at position at 22 is Gly, Asp, Glu, Gln, Asn, Lys, Arg, Cys, or Cysteic Acid;

Xaa at position 23 is His, Asp, Lys, Glu, or Gln;

Xaa at position 24 is Glu, His, Ala, or Lys;

Xaa at position 26 is Asp, Lys, Glu, or His;

Xaa at position 27 is Ala, Glu, His, Phe, Tyr, Trp, Arg, or Lys;

Xaa at position 31 is Ala, Glu, Asp, Ser, or His;

Xaa at position 33 is Asp, Arg, Val, Lys, Ala, Gly, or Glu;

Xaa at position 34 is Glu, Lys, or Asp;

Xaa at position 35 is Thr, Ser, Lys, Arg, Trp, Tyr, Phe, Asp, Gly, Pro, His, or Glu;

Xaa at position 36 is Arg, Glu, or His;

R is Lys, Arg, Thr, Ser, Glu, Asp, Trp, Tyr, Phe, His, —NH$_2$, Gly, Gly-Pro, or Gly-Pro-NH$_2$, or is deleted.

Another preferred group of GLP-1 compounds is comprised of GLP-1 analogs of formula V (SEQ ID NO:5):

```
  7    8    9   10   11   12   13   14   15   16   17
His-Xaa-Glu-Gly-Thr-Xaa-Thr-Ser-Asp-Xaa-Ser- 18   19   20   21   22   23   24   25   26   27   28
Ser-Tyr-Leu-Glu-Xaa-Xaa-Ala-Ala-Xaa-Glu-Phe- 29   30   31   32   33   34   35   36   37
Ile-Xaa-Trp-Leu-Val-Lys-Xaa-Arg-R
``` wherein:
  Xaa at position 8 is Gly, Ala, Val, Leu, Ile, Ser, or Thr;
  Xaa at position 12 is His, Trp, Phe, or Tyr;
  Xaa at position 16 is Leu, Ser, Thr, Trp, His, Phe, Asp, Val, Glu, or Ala;
  Xaa at position 22 is Gly, Asp, Glu, Gln, Asn, Lys, Arg, Cys, or Cysteic Acid;
  Xaa at position 23 is His, Asp, Lys, Glu, or Gln;
  Xaa at position 26 is Asp, Lys, Glu, or His;
  Xaa at position 30 is Ala, Glu, Asp, Ser, or His;
  Xaa at position 35 is Thr, Ser, Lys, Arg, Trp, Tyr, Phe, Asp, Gly, Pro, His, or Glu;
  R is: Lys, Arg, Thr, Ser, Glu, Asp, Trp, Tyr, Phe, His, —$NH_2$, Gly, Gly-Pro, or Gly-Pro-$NH_2$, or is deleted.

Another preferred group of GLP-1 compounds is comprised of GLP-1 analogs of formula VI (SEQ ID NO:6):

```
  7    8    9   10   11   12   13   14   15   16   17
His-Xaa-Glu-Gly-Thr-Phe-Thr-Ser-Asp-Val-Ser- 18   19   20   21   22   23   24   25   26   27   28
Ser-Tyr-Leu-Glu-Xaa-Xaa-Ala-Ala-Lys-Xaa-Phe- 29   30   31   32   33   34   35   36   37
Ile-Xaa-Trp-Leu-Val-Lys-Gly-Arg-R
``` wherein:
  Xaa at position 8 is Gly, Ala, Val, Leu, Ile, Ser, or Thr;
  Xaa at position 22 is Gly, Asp, Glu, Gln, Asn, Lys, Arg, Cys, or Cysteic Acid;
  Xaa at position 23 is His, Asp, Lys, Glu, or Gln;
  Xaa at position 27 is Ala, Glu, His, Phe, Tyr, Trp, Arg, or Lys
  Xaa at position 30 is Ala, Glu, Asp, Ser, or His;
  R is: Lys, Arg, Thr, Ser, Glu, Asp, Trp, Tyr, Phe, His, —$NH_2$, Gly, Gly-Pro, or Gly-Pro-$NH_2$, or is deleted.

Another preferred group of GLP-1 compounds is comprised of GLP-1 analogs of formula VII (SEQ ID NO:7):

```
  7    8    9   10   11   12   13   14   15   16   17
Xaa-Xaa-Glu-Gly-Thr-Phe-Thr-Ser-Asp-Val-Ser- 18   19   20   21   22   23   24   25   26   27   28
Ser-Tyr-Leu-Glu-Xaa-Gln-Ala-Ala-Lys-Glu-Phe- 29   30   31   32   33   34   35   36   37
Ile-Ala-Trp-Leu-Val-Lys-Gly-Arg-R
``` wherein:
  Xaa at position 7 is L-histidine, D-histidine, desamino-histidine, 2amino-histidine, β-hydroxy-histidine, homo-histidine, α-fluoromethyl-histidine or α-methyl-histidine;
  Xaa at position 8 is glycine, alanine, valine, leucine, isoleucine, serine or threonine. Preferably, Xaa at position 8 is glycine, valine, leucine, isoleucine, serine or threonine;
  Xaa at position 22 is aspartic acid, glutamic acid, glutamine, asparagine, lysine, arginine, cysteine, or cysteic acid.
  R is —$NH_2$ or Gly(OH).

Most preferred GLP-1 compounds of formula I, II, III, IV, V, VI, and VII comprise GLP-1 analogs wherein the backbone for such analogs or fragments contains an amino acid other than alanine at position 8 (position 8 analogs). Preferred amino acids at position 8 are glycine, valine, leucine, isoleucine, serine, threonine, or methionine and more preferably are valine or glycine. Even more preferred are GLP-1 compounds of formula I, II, III, IV, V, VI, and VII wherein not more than 6 amino acids differ from the corresponding amino acid in native GLP-1(7–37)OH, GLP-1(7–36)$NH_2$, or Exendin-4. Most preferred are GLP-1 compounds of formula I, II, III, IV, V, VI, and VII wherein between 1 and 5 amino acids differ from the corresponding amino acid in native GLP-1(7–37)OH, GLP-1(7–36)$NH_2$, or Exendin-4.

Other preferred GLP-1 compounds are GLP-1 analogs that have the sequence of GLP-1(7–37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine.

Other preferred GLP-1 compounds are GLP-1 analogs that have the sequence of GLP-1(7–37)OH except that the amino acid at position 8 is preferably glycine, valine, leucine, isoleucine, serine, threonine, or methionine and more preferably valine or glycine and position 30 is glutamic acid, aspartic acid, serine, or histidine and more preferably glutamic acid.

Other preferred GLP-1 compounds are GLP-1 analogs that have the sequence of GLP-1(7–37)OH except that the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

Other preferred GLP-1 compounds are GLP-1 analogs that have the sequence of GLP-1(7–37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 23 is lysine, arginine, glutamic acid, aspartic acid, and histidine and more preferably lysine or glutamic acid.

Other preferred GLP-1 compounds are GLP-1 analogs that have the sequence of GLP-1(7–37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 27 is alanine, lysine, arginine, tryptophan, tyrosine, phenylalanine, or histidine and more preferably alanine.

In the nomenclature used herein to describe GLP-1 compounds, the substituting amino acid and its position is indicated prior to the parent structure. For example $Val^8$-

GLP-1(7–37)OH designates a GLP-1 compound in which the alanine normally found at position 8 in GLP-1(7–37)OH is replaced with valine.

Other preferred GLP-1 compounds include: $Val^8$-GLP-1(7–37)OH, $Gly^8$-GLP-1(7–37)OH, $Glu^{22}$-GLP-1(7–37)OH, $Asp^{22}$-GLP-1(7–37)OH, $Arg^{22}$-GLP-1(7–37)OH, $Lys^{22}$-GLP-1(7–37)OH, $Cys^{22}$-GLP-1(7–37)OH, $Val^8$-$Glu^{22}$-GLP-1(7–37)OH, $Val^8$-$Asp^{22}$-GLP-1(7–37)OH, $Val^8$-$Arg^{22}$-GLP-1(7–37)OH, $Val^8$-$Lys^{22}$-GLP-1(7–37)OH, $Val^8$-$Cys^{22}$-GLP-1(7–37)OH, $Gly^8$-$Glu^{22}$-GLP-1(7–37)OH, $Gly^8$-$Asp^{22}$-GLP-1(7–37)OH, $Gly^8$-$Arg^{22}$-GLP-1(7–37)OH, $Gly^8$-$Lys^{22}$-GLP-1(7–37)OH, $Gly^8$-$Cya^{22}$-GLP-1(7–37)OH, $Glu^{22}$-GLP-1(7–36)$NH_2$, $Asp^{22}$-GLP-1(7–36)$NH_2$, $Arg^{22}$-GLP-1(7–36)$NH_2$, $Lys^{22}$-GLP-1(7–36)$NH_2$, $Cys^{22}$-GLP-1(7–36)$NH_2$, $Val^8$-$Glu^{22}$-GLP-1(7–36)$NH_2$, $Val^8$-$Asp^{22}$-GLP-1(7–36)$NH_2$, $Val^8$-$Arg^{22}$-GLP-1(7–36)$NH_2$, $Val^8$-$Lys^{22}$-GLP-1(7–36)$NH_2$, $Val^8$-$Cys^{22}$-GLP-1(7–36)$NH_2$, $Gly^8$-$Glu^{22}$-GLP-1(7–36)$NH_2$, $Gly^8$-$Asp^{22}$-GLP-1(7–36)$NH_2$, $Gly^8$-$Arg^{22}$-GLP-1(7–36)$NH_2$, $Gly^8$-$Lys^{22}$-GLP-1(7–36)$NH_2$, $Gly^8$-$Cys^{22}$-GLP-1(7–36)$NH_2$, $Lys^{23}$-GLP-1(7–37)OH, $Val^8$-$Lys^{23}$-GLP-1(7–37)OH, $Gly^8$-$Lys^{23}$-GLP-1(7–37)OH, $His^{24}$-GLP-1(7–37)OH, $Val^8$-$His^{24}$-GLP-1(7–37)OH, $Gly^8$-$His^{24}$-GLP-1(7–37)OH, $Lys^{24}$-GLP-1(7–37)OH, $Val^8$-$Lys^{24}$-GLP-1(7–37)OH, $Gly^8$-$Lys^{23}$-GLP-1(7–37)OH, $Glu^{30}$-GLP-1(7–37)OH, $Val^8$-$Glu^{30}$-GLP-1(7–37)OH, $Gly^8$-$Glu^{30}$-GLP-1(7–37)OH, $Asp^{30}$-GLP-1(7–37)OH, $Val^8$-$Asp^{30}$-GLP-1(7–37)OH, $Gly^8$-$Asp^{30}$-GLP-1(7–37)OH, $Gln^{30}$-GLP-1(7–37)OH, $Val^8$-$Gln^{30}$-GLP-1(7–37)OH, $Gly^8$-$Gln^{30}$-GLP-1(7–37)OH, $Tyr^{30}$-GLP-1(7–37)OH, $Val^8$-$Tyr^{30}$-GLP-1(7–37)OH, $Gly^8$-$Tyr^{30}$-GLP-1(7–37)OH, $Ser^{30}$-GLP-1(7–37)OH, $Val^8$-$Ser^{30}$-GLP-1(7–37)OH, $Gly^8$-$Ser^{30}$-GLP-1(7–37)OH, $His^{30}$-GLP-1(7–37)OH, $Val^8$-$His^{30}$-GLP-1(7–37)OH, $Gly^8$-$His^{30}$-GLP-1(7–37)OH, $Glu^{34}$-GLP-1(7–37)OH, $Val^8$-$Glu^{34}$-GLP-1(7–37)OH, $Gly^8$-$Glu^{34}$-GLP-1(7–37)OH, $Ala^{34}$-GLP-1(7–37)OH, $Val^8$-$Ala^{34}$-GLP-1(7–37)OH, $Gly^8$-$Ala^{34}$-GLP-1(7–37)OH, $Gly^{34}$-GLP-1(7–37)OH, $Val^8$-$Gly^{34}$-GLP-1(7–37)OH, $Gly^8$-$Gly^{34}$-GLP-1(7–37)OH, $Ala^{35}$-GLP-1(7–37)OH, $Val^8$-$Ala^{35}$-GLP-1(7–37)OH, $Gly^8$-$Ala^{35}$-GLP-1(7–37)OH, $Lys^{35}$-GLP-1(7–37)OH, $Val^8$-$Lys^{35}$-GLP-1(7–37)OH, $Gly^8$-$Lys^{35}$-GLP-1(7–37)OH, $His^{35}$-GLP-1(7–37)OH $Val^8$-$His^{35}$-GLP-1(7–37)OH, $Gly^8$-$His^{35}$-GLP-1(7–37)OH, $Pro^{35}$-GLP-1(7–37)OH, $Val^8$-$Pro^{35}$-GLP-1(7–37)OH, $Gly^8$-$Pro^{35}$-GLP-1(7–37)OH, $Glu^{35}$-GLP-1(7–37)OH $Val^8$-$Glu^{35}$-GLP-1(7–37)OH, $Gly^8$-$Glu^{35}$-GLP-1(7–37)OH, $Val^8$-$Ala^{27}$-GLP-1(7–37)OH, $Val^8$-$His^{37}$-GLP-1(7–37)OH, $Val^8$-$Glu^{22}$-$Lys^{23}$-GLP-1(7–37)OH, $Val^8$-$Glu^{22}$-$Glu^{23}$-GLP-1(7–37)OH, $Val^8$-$Glu^{22}$-$Ala^{27}$-GLP-1(7–37)OH, $Val^8$-$Gly^{34}$-$Lys^{35}$-GLP-1(7–37)OH, $Val^8$-$His^{37}$-GLP-1(7–37)OH, and $Gly^8$-$His^{37}$-GLP-1(7–37)OH.

More preferred GLP-1 compounds are $Val^8$-GLP-1(7–37)OH, $Gly^8$-GLP-1(7–37)OH, $Glu^{22}$-GLP-1(7–37)OH, $Lys^{22}$-GLP-1(7–37)OH, $Val^8$-$Glu^{22}$-GLP-1(7–37)OH, $Val^8$-$Lys^{22}$-GLP-1(7–37)OH, $Gly^8$-$Glu^{22}$-GLP-1(7–37)OH, $Gly^8$-$Lys^{22}$-GLP-1(7–37)OH, $Glu^{22}$-GLP-1(7–36)$NH_2$, $Lys^{22}$-GLP-1(7–36)$NH_2$, $Val^8$-$Glu^{22}$-GLP-1(7–36)$NH_2$, $Val^8$-$Lys^{22}$-GLP-1(7–36)$NH_2$, $Gly^8$-$Glu^{22}$-GLP-1(7–36)$NH_2$, $Gly^8$-$Lys^{22}$-GLP-1(7–36)$NH_2$, $Val^8$-$His^{37}$-GLP-1(7–37)OH, $Gly^8$-$His^{37}$-GLP-1(7–37)OH, $Arg^{34}$-GLP-1(7–36)$NH_2$, and $Arg^{34}$-GLP-1(7–37)OH.

GLP-1 compounds of the present invention also include GLP-1 derivatives. A GLP-1 derivative is defined as a molecule having the amino acid sequence of GLP-1 or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist. The α-carbon of an amino acid may be mono- or dimethylated. A preferred GLP-1 derivative is $Arg^{34}Lys^{26}$-(N-ε-(γ-Glu (N-α-hexadecanoyl)))-GLP-1 (7–37).

Numerous published applications describe derivatives of GLP-1, GLP-1 analogs, Exendin-4, and Exendin-4 analogs. See U.S. Pat. No. 5,512,540, WO96/29342, WO98/08871, WO99/43341, WO99/43708, WO99/43707, WO99/43706, and WO99/43705 which are herein incorporated by reference in their entirety.

"Basic polypeptides" include but are not limited to basic proteins or polyamines. Examples of basic proteins or polyamines are polylysine, polyarginine, polyornithine, protamine, putrescine, spermine, spermidine, and histone. Preferred basic polypeptides are polyarginine, protamine, polylysine, polyaspartic acid, polyglutamic acid, and polyornithine. More preferred is polylysine, polyarginine, and protamine. Most preferred is protamine. Protamine is the generic name of a group of strongly basic proteins present in sperm cell nuclei in salt like combination with nucleic acids. Commercially available protamines can be isolated from mature fish sperm and are usually obtained as the sulfate. The peptide composition of a specific protamine may vary depending on which family, genera or species of fish it is obtained from. Protamine from salmon or trout can be separated into two, three, or more main fractions of proteins that may be separated further. The different parent peptides consist of about 30 amino acids of which more than 20 are arginines. The average molecular weight of protamine is about 4,300. Commercially available protamine sulfate is approximately 80% protamine.

The word "particle" in the present specification refers to a solid material complex comprising a GLP-1 compound and a basic polypeptide. The particles optionally comprise divalent metal ions. The particles are comprised of either crystalline or amorphous material or a mixture of crystalline and amorphous material. A crystalline particle of the present specification is a particle comprised primarily of individual or clusters of microcrystals, rods, needles, or plates or mixtures thereof. Preferably, the crystalline particles are comprised of small clusters of plate-like microcrystals. Most preferably the crystalline particles are homogeneous in size and shape (unimodal) and appear as small clusters of plate-like microcrystals. The particles of the present invention have a number diameter that ranges from about 0.5 μm to about 12 μm. It is preferable that particles have a number diameter that ranges from about 1 μm to about 5 μm. More preferably, the particles have a number diameter that ranges from about 1 μm to about 3 μm. The number mean diameter of the preferred crystalline particles in a composition is from about 1 μm to about 5 μm. More preferably, the number mean diameter of the preferred crystalline particles in a composition is from about 1 μm to about 3 μm. More preferably, the number mean diameter of the preferred crystalline particles in a composition is from about 3 μm to about 5 μm. More preferably, the number mean diameter of the preferred crystalline particles in a composition is from about 4 μm to about 5 μm. More preferably, 90% of the particles in the composition are less than 12 μm. More preferably, 90% of the particles in the composition are less than 9 μm, most preferably less than 7 μm. The number diameters were determined using a Coulter Multisizer II (Coulter Electronics Limited, Luton, Beds, England). The Coulter Multisizer uses an electrical sensing zone technique. Particle size, volume, and surface area distributions are calculated based on measurable changes in electrical resistance produced by non-conductive particles suspended in an electrolyte.

An amorphous particle for the purposes of the present invention refers to a particle comprising a precipitate, but lacking matter in a crystalline state and a definable form or structure as determined by polarized light microscopy.

The present invention encompasses particles formed from a GLP-1 compound and a basic polypeptide added together at a ratio between about 4:1 and about 10:1 (weight per weight) (w/w), preferably at a ratio between about 5:1 and about 10:1 (w/w), more preferably at a ratio between about 6:1 and about 10:1 (w/w), and most preferably at a ratio between about 7:1 and about 9:1 (w/w)(GLP-1 compound: basic polypeptide).

Additionally, the present invention may encompass a mixture of particle preparations wherein particles formed from mixing, precipitating, or crystallizing a GLP-1 compound and a basic polypeptide at one ratio are mixed with particles formed from mixing, precipitating, or crystallizing a GLP-1 compound and a basic polypeptide at another ratio.

The word "solubility" means the amount of GLP-1 compound in particle form that will dissolve in phosphate buffered saline (PBS) in a given period of time. A dried particle preparation is suspended in phosphate buffered saline (PBS) such that the final concentration of GLP-1 compound is 1 mg/mL or alternatively a concentrated GLP-1 particle suspension such as that described in examples 1 and 2 is diluted with PBS such that the final concentration of GLP-1 compound is 1 mg/mL. The resulting suspension is gently stirred for one hour at room temperature. Solubility is then determined by measuring the concentration of the GLP-1 compound in the supernatant by UV absorbance measurements. The solubility range for the particles of the present invention in PBS ranges from about 0.5 mg/ml to about 0.1 mg/ml.

Optionally, the particles of the present invention further comprise a divalent metal ion such as zinc. Preferably zinc is present at a molar ratio of less than about 2:1 (Zn:GLP-1 compound). Most preferably, zinc is present at a molar ratio of about 1:6 to about 1:1 (Zn:GLP-1 compound). The addition of zinc decreases the solubility of the particles to less than 0.2 mg/ml and in some cases less than 0.1 mg/ml.

The particles described above may be prepared as a suspension or as a dried powder. Dry powders of the present invention are formed from a suspension or solution of GLP-1 compound and basic polypeptide and optionally zinc.

Preparation of the Particles in a Suspension.

The particles of the present invention may be prepared by mixing a GLP-1 compound solution with a basic polypeptide solution. A GLP-1 compound solution is preferably a buffered solution and is prepared by dissolving GLP-1 compound in a selected buffer. Examples of a buffer include but are not limited to TRIS, Glycine, Arginine, and Phosphate. A preferred buffer is TRIS. The concentration of buffer should be such that changes in hydrogen ion concentration that would otherwise occur as a result of chemical reactions are minimized. The pH of the GLP-1 solution is about pH 6 to about pH 10, preferably about pH 7 to about pH 10, more preferably about pH 8 to about pH 10, and most preferably about pH 9 to about pH 10. The pH of the GLP-1 compound solution can be adjusted based on the isoelectric point (pI) of the GLP-1 compound being dissolved to optimize the amount of GLP-1 compound that will dissolve and remain soluble in the buffered GLP-1 solution. For example, it is preferable that Val$^8$-GLP-1(7–37)OH be dissolved in a TRIS buffered solution wherein the pH is adjusted to 9.0.

The basic polypeptide solution is preferably a buffered solution prepared by dissolving a basic polypeptide in a selected buffer. Examples of a buffer include but are not limited to TRIS, Glycine, Arginine, and Phosphate. A preferred buffer is TRIS. The concentration of buffer should be such that changes in hydrogen ion concentration that would otherwise occur as a result of chemical reactions are minimized. The pH of the buffered basic polypeptide solution is about pH 6 to about pH 10, preferably about pH 7 to about pH 10, more preferably about pH 8 to about pH 10, and most preferably about pH 9 to about pH 10. The concentration of basic polypeptide in solution is about 1.0 to about 20.0 mg/mL. However, ultimately, the concentration of basic polypeptide will be such that when the basic polypeptide solution is added to the GLP-1 compound solution the desired ratio of GLP-1 compound to basic polypeptide is achieved. For example, it is preferable that protamine is dissolved in a Tris buffered solution at a pH of 9.0.

To induce particle formation and reduce adhesion of the particles to reaction vessels, an alcohol selected from the group consisting of ethanol, propanol, isopropanol, and methanol, or mixtures thereof, is added to either the buffered GLP-1 compound solution, the buffered basic polypeptide solution, or both solutions. It is preferred that the final concentration of alcohol once the buffered GLP-1 compound solution and the buffered basic polypeptide solution are mixed is between about 0.2 and about 10% (volume to volume) (v/v). Most preferred is an ethanol concentration between about 4% and 5% (v/v).

The particles of the present invention are prepared by mixing a buffered GLP-1 compound solution with a buffered basic polypeptide solution. A suspension of amorphous precipitate is initially formed. However, if primarily crystalline particles are desired, the suspension is incubated for about 18 to 24 hours. Although the temperature of incubation is not critical, it is preferable that the temperature be between about 5° C. and about 35° C. to avoid denaturation of the peptide and to preserve the crystalline matrix that forms. Preferably, the temperature is about 25° C. The amount of time and temperature of incubation can be varied depending on whether amorphous particles, crystalline particles, or a mixture of amorphous and crystalline particles are desired.

The amount of the GLP-1 solution and the basic peptide solution to be mixed together may be adjusted depending on the concentration of GLP-1 compound and basic polypeptide and alcohol in each solution such that the ratios of GLP-1 compound to basic polypeptide in the final mixture range from about 4:1 to about 10:1 (w/w). Surprisingly, the final ratio of GLP-1 compound to basic polypeptide affects particle morphology as well as the ultimate yield of particles in suspension.

For example, a ratio that generally results in crystalline particles comprised of individual and clusters of microcrystals, rods, needles, plates or mixtures thereof is about 5:1 (w/w) (GLP-1 compound:basic polypeptide), whereas a ratio of 4:1 (w/w) (GLP-1 compound:basic polypeptide) additionally results in larger clusters of microcrystals, rods, needles, and plates. Although these types of crystals can be formulated in a pharmaceutical composition for injectable type therapy, they generally are not as suitable for pulmonary delivery as the smaller crystals that are formed from higher GLP-1 compound to basic polypeptide ratios.

The yield of particle formation at ratios between about 4:1 and about 5:1 (w/w of GLP-1 compound to basic polypeptide) is generally near 100%. However, it is even more preferred that the ratio of GLP-1 compound to basic polypeptide be increased to above 5:1 (GLP-1 compound:basic polypeptide) even though this results in a decreased yield. The resulting particles at higher GLP-1 compound to basic polypeptide ratios are typically smaller and thus, more suitable for pulmonary delivery.

Preferably, the concentrations of GLP-1 compound in the GLP-1 solution and basic polypeptide in the basic polypeptide solution are adjusted such that the ratios of GLP-1 compound to basic polypeptide range from about 6:1 to about 10:1 (w/w), and more preferably from about 7:1 to about 9:1 (w/w)(GLP-1 compounds:basic polypeptide). The yield of particle formation at these ratios is less than 95%, usually less than 90%. Preferably, the yield of particles is between about 85% and about 75% (See Example 3). For example, as the yield of precipitated Val$^8$-GLP-1(7–37)OH is decreased, i.e. less protamine relative to the amount of GLP-1 is added, the particle size decreases such that a larger portion of the particles have a number diameter between about 1 μm and about 3 μm.

In another embodiment, a divalent metal ion such as zinc is added to the suspension of GLP-1/protamine particles (see Example 13) to improve the yield and change the solubility properties of GLP-1 compound particles. The solubility characteristics of the particles of the present invention can be effected depending on the amount of zinc added relative to the amount of GLP-1 compound present. Such a method for controlling the solubility characteristics is useful because the solubility characteristics of the particle determine the drug release rate at the site of delivery. Hence by controlling the solubility characteristics, one can control the pharmacokinetic properties of the drug. Furthermore, soaking the suspension of particles in a solution of zinc can drive the particle formation to completion (i.e., near 100%) (see Example 13).

Zinc is preferably added as a salt. Representative examples of zinc salts include zinc acetate, zinc bromide, zinc chloride, zinc fluoride, zinc iodide and zinc sulfate. The skilled artisan will recognize that there are many other zinc salts that also might be used to make the particles of the present invention. Preferably, zinc oxide, zinc acetate or zinc chloride is used. Preferably, a buffered zinc solution at pH of between about 5 and about 6 can be added to the suspension of GLP-1 compound/basic polypeptide particles. A preferred buffer for the buffered zinc solution is glycine. More preferably, an acidic zinc solution at pH of between about 1 and about 2 can be added to the suspension of particles. The preferred final molar ratio of zinc to GLP-1 compound is less than about 2:1. Although the temperature of incubation is not critical, the suspension is generally incubated in the presence of zinc between about 18 and about 24 hours at a temperature between about 5° C. and about 25° C.

Thus, the preferred particles of the present invention are prepared by mixing a buffered GLP-1 compound solution with a buffered basic polypeptide solution and an alcohol such that the ratio of GLP-1 compound to basic polypeptide is greater than 4:1 (w/w), preferably greater than 5:1 and the concentration of alcohol is between about 0.2% and about 10% (v/v), preferably between about 4% and about 5% (v/v). It is preferred that initially the yield of particles be between about 80% and 95%. To drive particle yield to 100% and to decrease the solubility of the particles, zinc is added at a molar ratio that is less than 2:1 (Zinc:GLP-1 compound).

The resulting suspension of particles may comprise a small amount of uncomplexed GLP-1 compound, uncomplexed basic polypeptide, and uncomplexed zinc depending on the yield of particles and the amount of each added, as well as a comparatively larger amount of particles containing GLP-1 compound complexed with basic polypeptide, particles containing GLP-1 compound complexed with metal ion, and particles containing GLP-1 compound complexed with both metal ion and basic polypeptides.

The suspension of particles can be used as a composition suitable for subcutaneous or other types of injectable therapy. The injectable pharmaceutical compositions of the present invention may comprise a pharmaceutically acceptable preservative. Preservatives may be added to the pharmaceutical compositions of the present invention to prevent microbial contamination. Examples of preservatives include benzyl alcohol, phenol, chlorocresol, m-cresol, o-cresol, p-cresol, ethylparaben, methylparaben, propylparaben, butylparaben and thymol, and mixtures thereof. More preferred preservatives are benzyl alcohol, m-cresol, phenol, methylparaben and mixtures thereof. A most preferred preservative is m-cresol.

Alternatively the suspension can be manipulated to form a solution which can then be administered as an injectable composition or as an aerosol or spray-dried to a dry powder, composition of particles. If a solution is desired, the suspension of particles can be dissolved by adjusting the pH of the suspension. Typically the pH is decreased until the particles dissolve. Generally, adjustment of the pH to less than 6 will result in dissolution of the particles. More preferred is a pH of less than 5. Most preferred is a pH less than 4. The result is a solution formulation that precipitates upon administration. The precipitate forms as the solution is exposed to physiological pH. Surprisingly, the particles which reform as part of the precipitate retain the solubility properties of the particles in suspension which provide a protracted time action.

The suspension of particles or the solution described herein can be used or adapted for use as a composition delivered as an aerosol through the pulmonary route. A variety of inhalation devices are known in the art for pulmonary administration of an aerosol. These devices include metered dose inhalers, nebulizers, sprayers, and the like.

The suspension or the solution of the present invention can be formulated to be used in metered dose inhaler (MDI). In a MDI, a propellant, the suspension or the solution, and any excipients or other additives are contained in a canister as a mixture including a liquefied compressed gas. The propellant may be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. A surfactant can be chosen to stabilize the suspension or solution in the propellant, to protect the active agent against chemical degradation, and the like. Suitable surfactants include sorbitan trioleate, soya lecithin, oleic acid, or the like. In some cases solution aerosols are prepared using solvents such as ethanol.

The suspension or the solution of the present invention can be formulated to be used in a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws the suspension or solution through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation either directly or through a coupling fluid, creating an aerosol. The suspension or solution may also include agents such as an excipient, a buffer, an isotonicity agent, a preservative, a surfactant, and a stabilizing agent. Stabilizing agents include a reducing agent, a bulk protein, or a carbohydrate. Bulk proteins include albumin. Typical carbohydrates include sucrose, mannitol, lactose, trehalose, glucose, or the like. Surfactants can reduce or prevent surface-induced aggregation of the GLP-1 compound complexes caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan monooleate, polysorbate 80, polysorbate 20, or the like.

The suspension or the solution of the present invention can be formulated to be used in a sprayer by forcing a suspension or solution through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. The suspension or solution may also include agents such as an excipient, a buffer, an isotonicity agent, a preservative, a surfactant, and a stabilizing agent.

Advantageously, particles delivered by a MDI, nebulizer, or sprayer have a particle size less than about 10 µm, preferably in the range of about 1 µm to about 5 µm.

Preferably, however, the suspension of particles or the solution as described herein is further manipulated to provide a dry powder composition of particles suitable for pulmonary delivery in a dry powder inhaler.

Preparation of Spray Dried Powder

A preferred embodiment of the present invention is a dry powder formed from the GLP-1 compound complexed with a basic polypeptide in a suspension or solution described herein. Preferably, a dry powder can be prepared by spray drying the suspension of particles or the solution of dissolved particles. Spray dried powder can be prepared using a Büchi 191 lab top spray dryer. The suspension or solution can be spray dried at an inlet temperature of between about 120° C. and about 200° C. The outlet temperature is between about 50° C. and about 110° C. during the drying process. The aspiration setting is between about 20 mbar and about 60 mbar, nitrogen flow is between about 400 L/hr and about 600 L/hr, and feed is between about 3 mL/min and 8 mL/min. The powder can be collected by a collector or a cyclone. To obtain powder with good dispersion characteristics the inlet drying temperature is about 200° C. Other spray drying parameters include nitrogen flow at about 600 L/hr, an aspiration rate of nitrogen between about 80% and about 100% and the sample introduction flow rate or feed at about 5 mL/min.

Preferably, the suspension of particles or the solution of dissolved particles is diluted prior to spray drying such that the final concentration of GLP-1 compound is less than 8 mg/mL. The diluent can be water, buffer, bulking agent, carrier, excipient, another additive, or the like. Additives can be included in the dry powder to dilute the powder as required for delivery from the particular powder inhaler, to facilitate processing of the formulation, to provide advantageous powder properties to the formulation, to facilitate dispersion of the powder from the inhalation device, to stabilize the formulation (e.g., antioxidants or buffers), to provide taste to the formulation, or the like. Advantageously, the additive does not adversely affect the patient's airways. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; amino acids, such as arginine, glycine, and leucine; or the like. Typically an additive, such as a bulking agent, is present in an amount effective for a purpose described above, often at about 50% to about 90% by weight of the formulation.

Surprisingly, use of an amino acid in the suspension or solution prior to spray drying maximizes dispersion and allows the inlet temperature to be decreased from 200° C. to about 120° C. This reduction in temperature reduces the thermal stress on the GLP-1 compound and provides greater stability. Preferred amino acids for maximizing dispersion and permitting a reduction in the inlet temperature during the drying process are glycine and leucine. More preferred is leucine at a ratio of between 3:1 to 1:3 (w/w) (GLP-1 compound:leucine).

Alternatively; dry powder can be obtained by drying, by filtration or freeze drying. Drying by filtration can be performed as described in example 20. GLP-1 compound particle suspensions can be filtered through a glass filter and washed with alcohol. The particles dry at room temperature under mild vacuum. Freeze drying can be performed as described in example 21. GLP-1 compound particle suspensions can be frozen using an alcohol dry ice bath. The frozen suspension is then dried under vacuum for a time sufficient to dry the particles.

Preferably, the dried powders can be used or adapted for use as a composition delivered by dry powder inhalers through the pulmonary route. Advantageously for administration by the pulmonary route, the dry powders have a preferred aerodynamic particle size of less than about 10 µm, more preferably about 1 µm to about 5 µm, and most preferably about 3 µM to about 5 µm as measured using an aerosizer. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 µm. The dry powder can also be characterized as having a geometric particle size of about 4 µm to about 18 µm as measured by laser diffraction. The true density of the dry powders is between about 1.25 g/cc and 1.45 g/cc. The solubility of the dried powder in PBS ranges from about 0.5 mg/ml to about 0.05 mg/ml.

The pharmaceutical compositions of the present invention may be used to treat or may be manufactured for use as a medicament for the treatment of diabetes, hyperglycemia, obesity (see WO 98/19698), irritable bowel syndrome (see WO 99/64060), or to reduce the morbidity and mortality associated with myocardial infarction (see WO 98/08531) and stroke (see WO 00/16797) as well as catabolic changes that occur after surgery (see U.S. Pat. No. 6,006,753), or related conditions in mammals such as humans. Also included are subjects at risk for developing non-insulin dependent diabetes (see WO 00/07617).

Side effects that have been observed when GLP-1 is administered include nausea and vomiting. This is thought to be due to the initial peak levels of the compound that are obtained immediately after administration. In order for a short acting formulation to provide a therapeutic benefit, it must be injected at a high enough dose to provide blood levels that are in the therapeutic range at least long enough to achieve a glucose lowering effect after a meal. Thus far, this has only been achieved by administering GLP-1 wherein fairly high peak levels of the drug are achieved.

Upon administration, the composition of particles provide extended in vivo half-life and slow in vivo clearance of the GLP-1 compound from circulation. Further, the composition of particles encompassed by the present invention provide a protracted time action wherein GLP-1 maintains a fairly flat serum profile for longer than 8 hours after pulmonary delivery in monkeys. Pulmonary delivery of the particles of the present invention is not associated with a sharp peak of GLP-1 in the serum following administration and thus, avoids side effects such as nausea and vomiting. In addition, a suspension of particles administered by intratracheal instillation to rats resulted in relatively constant detectable blood levels of GLP-1 compound for at least 6 hours post-administration (see Example 15 and 16).

Doses of the compositions of the present invention depend on the potency and bioavailability of the GLP-1 compound in the particular composition. Generally, when delivered by the pulmonary route, the compositions of the present invention will have a bioavailability that is approximately 10% to 50% that of the compound delivered subcutaneously. However, an enhancer such as diketopiperazine may be added to further increase bioavailability after pulmonary administration.

A dose range of approximately 0.001 mg to about 2 mg of a GLP-1 compound within the pharmaceutical compositions of the present invention per kg of body weight of a mammal may be administered to the mammal in need of such treatment. One skilled in the art will recognize that smaller or larger doses may also be operable, depending on the patient, their condition and the manner of administration and the particular serum levels that must be achieved. Preferred dose ranges include 0.001 to 1 mg/kg, 0.01 to 1 mg/kg, 0.01 to 0.1 mg/kg, and 0.2 to 0.8 mg/kg. More preferred dose ranges include 0.001 to 1 mg/kg, 0.005 to 1 mg/kg, 0.01 to 1 mg/kg, and 0.01 to 0.5 mg/kg.

A total dose range of about 0.01 mg to about 20 mg, based on the mass of the particles in the pharmaceutical compositions of the present invention, may be administered to a mammal, such as a human, in need of such treatment. One skilled in the art will recognize that a smaller or larger total dose may also be operable, depending on the patient, their condition and the manner of administration. Preferred total dose ranges include 0.01 mg to 10 mg, 0.1 to 10 mg, 1 to 8 mg and 2 to 6 mg. More preferred total dose ranges are 1 to 8 mg and 2 to 6 mg.

The composition of particles encompassed by the present invention have a duration of action when delivered pulmonarily that is longer than 8 hours as observed in monkeys. Thus, a method of administering the compositions of the present invention through the pulmonary route involves administration of the appropriate dose most preferably once per day. Administration may also be twice per day or three times per day and may be associated with meals. Additionally, a method of treatment using the compositions of the present invention may involve administration once, twice, or three times a day followed by administration in the evening before bedtime.

EXAMPLE 1

$Val^8$-GLP-1 Protamine Particles

A 12.1 ml buffered $Val^8$-GLP-1(7–37)OH solution was prepared by dissolving $Val^8$-GLP-1 in a 20 mM TRIS buffer solution to achieve a final concentration of 4 mg/ml $Val^8$-GLP-1. The pH was adjusted to 9.0 with 1N NaOH and the resulting solution was filtered.

A 10 ml buffered protamine sulfate solution was prepared by dissolving protamine sulfate in a 20 mM TRIS buffer solution to achieve a final concentration of 0.6 mg/mL of protamine. The pH was adjusted to 9.0 with 5N HCl. Absolute ethanol was added to the buffered protamine sulfate solution to a concentration of 5%, (v/v) (0.05 mL of absolute ethanol was added to 1 mL of buffered protamine sulfate solution). The resulting solution was filtered and 1 mL was added to 1 mL of $Val^8$-GLP-1(7–37)OH solution and incubated at 25° C. After 24 hours, a suspension of particles comprising $Val^8$-GLP-1 and protamine formed. The yield was determined by measuring the amount of $Val^8$-GLP-1 in the supernatant versus the total amount of $Val^8$-GLP-1 in the reaction and was approximately 90% to 95%. Polarized light microscopy revealed particles comprised of small clusters of plate-like crystals. The number mean diameter of the particles was 4.1 μm with 90% less than 7.7 μm as determined by Coulter Multisizer II (Coulter Electronics Limited, Luton, Beds, England). Typically the suspension is diluted 250 fold into the electrolyte medium for measurement. The particles are counted and sized as they pass through a small orifice located between two electrodes. The change in resistance is directly proportional to the volume of the particle and the number of pulses at a given size produces a size distribution. The size is calculated as the diameter of an equivalent sphere with the same volume detected. The instrument is calibrated by particle size standard which is composed of spherical particles.

EXAMPLE 2

$Val^8$-GLP-1 Protamine Particles

A buffered $Val^8$-GLP-1(7–37)OH solution was prepared by dissolving two grams $Val^8$-GLP-1 in 230 mL of 20 mM TRIS buffer solution. The pH was adjusted to 9.5 with 1N NaOH and the resulting solution was filtered. The $Val^8$-GLP-1(7–37)OH was determined by UV measurements to be 6.3 mg/mL.

A buffered protamine sulfate solution was prepared by dissolving 1.216 μm of protamine sulfate in 400 mLs of water for a final concentration of 3.04 mg/mL. The approximate protamine concentration is 80% of the protamine sulfate concentration. Therefore, the protamine concentration is approximately 2.4 mg/mL. 85 mLs of the protamine sulfate solution was diluted with 126 mLs of water, and 9.6 mLs of 0.5 M TRIS buffer solution, and 19.2 mLs of absolute ethanol for a final protamine concentration of approximately 0.85 mg/mL. The pH was adjusted to 9.6 with 5N NaOH, and the resulting solution was filtered.

About 230 mLs of the $Val^8$-GLP-1(7–37)OH solution was combined with about 230 mLs of the protamine solution at 25° C. After 24 hours, a suspension of particles comprising $Val^8$-GLP-1 and protamine formed. Polarized light microscopy revealed particles comprised of small clusters of plate-like crystals. The number mean diameter of the particles was 3.4 μm with 90% less than 6.2 μm as determined by Coulter Multisizer II (Coulter Electronics Limited, Luton, Beds, England).

EXAMPLE 3

$Val^8$-GLP-1 Protamine Particles Formed using Different Ratios.

Separate $Val^8$-GLP-1 and protamine solutions were prepared as in example 1. Different volumes of the solutions were then combined to obtain different $Val^8$-GLP-1:protamine ratios. The effect of using different ratios of GLP-1 compound and protamine on the particle yield are displayed in the following table.

|  | $Val^8$-GLP-1 | Protamine | Ratio | Yield % |
| --- | --- | --- | --- | --- |
| Example 1 | 2.0 mg | 0.55 mg | 3.6 | 99.4 |
| Example 2 | 2.0 mg | 0.49 mg | 4.1 | 99.7 |
| Example 3 | 2.0 mg | 0.44 mg | 4.5 | 99.5 |
| Example 4 | 2.0 mg | 0.38 mg | 5.3 | 98.3 |
| Example 5 | 2.0 mg | 0.33 mg | 6.1 | 94.5 |
| Example 6 | 2.0 mg | 0.27 mg | 7.4 | 84.3 |
| Example 7 | 2.0 mg | 0.22 mg | 9.1 | 73.2 |
| Example 8 | 2.0 mg | 0.16 mg | 12.5 | 54.6 |

The yields were determined as described in Example 1.

EXAMPLE 4

$Val^8$-GLP-1 poly-L-arginine Particles

A $Val^8$-GLP-1 solution was prepared as in example 1.

A 6.8 mL poly-L-arginine solution was prepared by dissolving poly-L-arginine in a 20 mM TRIS buffer solution to achieve a final concentration of 1.2 mg/mL. The pH was adjusted to 9.2 with 5N NaOH.

Absolute ethanol was added to the poly-L-arginine solution to a concentration of 7% (v/v)(0.07 mL of absolute ethanol was added to 1 mL of buffered protamine sulfate solution). The resulting solution was filtered and added to 1 mL of $Val^8$-GLP-1(7–37)OH solution and incubated at 25° C. After 24 hours, a suspension of particles comprising $Val^8$-GLP-1 and poly-L-arginine formed. The yield was determined as described in Example 1 and was about 90%. Polarized light microscopy revealed particles comprised of small clusters of plate-like crystals. The number mean diameter of the particles was 2.7 μm with 90% less than 5.1 μm as determined by Coulter Multisizer II (Coulter Electronics Limited, Luton, Beds, England).

EXAMPLE 5

$Val^8$-$Glu^{22}$-GLP-1 Protamine Particles

A 0.5 mL buffered $Val^8$-$Glu^{22}$-GLP-1 solution was prepared by dissolving $Val^8$-$Glu^{22}$-GLP-1 in a 20 mM TRIS buffer solution to achieve a final concentration of approximately 10 mg/ml $Val^8$-$Glu^{22}$-GLP-1. The pH was adjusted to 9.5 with 1N NaOH and the resulting solution was filtered.

A 1.2 mg/mL buffered protamine sulfate solution containing ethanol was prepared as described in example 1 and 0.5 mL was added to the 0.5 mL buffered $Val^8$-$Glu^{22}$-GLP-1 solution and incubated at 25° C. After 24 hours, a suspension of particles comprising $Val^8$-$Glu^{22}$-GLP-1 and protamine formed.

EXAMPLE 6

$Val^8$-$Lys^{22}$-GLP-1 Protamine Particles

A 0.5 mL buffered $Val^8$-$Lys^{22}$-GLP-1 solution was prepared by dissolving $Val^8$-$Lys^{22}$-GLP-1 in a 20 mM TRIS buffer solution to achieve a final concentration of approximately 8 mg/ml $Val^8$-$Lys^{22}$-GLP-1. The pH was adjusted to 9.3 with 1N NaOH and the resulting solution was filtered.

A 1.2 mg/mL buffered protamine sulfate solution containing ethanol was prepared as described in example 1 and 0.5 mL was added to the 0.5 mL buffered $Val^8$-$Lys^{22}$-GLP-1 solution and incubated at 25° C. After 24 hours, a suspension of particles comprising $Val^8$-$Lys^{22}$-GLP-1 and protamine formed.

EXAMPLE 7

$Gly^8$-GLP-1 Protamine Particles

A 0.5 mL buffered $Gly^8$-GLP-1 solution was prepared by dissolving $Gly^8$-GLP-1 in a 20 mM TRIS buffer solution to achieve a final concentration of approximately 8 mg/ml $Gly^8$-GLP-1. The pH was adjusted to 9.3 with 1N NaOH and the resulting solution was filtered.

A 1.2 mg/mL buffered protamine sulfate solution containing ethanol was prepared as described in example 1 and 0.5 mL was added to the 0.5 mL buffered $Gly^8$-GLP-1 solution and incubated at 25° C. After 24 hours, a suspension of particles comprising $Gly^8$-GLP-1 and protamine formed.

EXAMPLE 8

$Val^8$-$Glu^{30}$-GLP-1 Protamine Particles

A 0.5 mL buffered $Val^8$-$Glu^{30}$-GLP-1 solution was prepared by dissolving $Val^8$-$Glu^{30}$-GLP-1 in a 20 mM TRIS buffer solution to achieve a final concentration of approximately 8 mg/ml $Val^8$-$Glu^{30}$-GLP-1. The pH was adjusted to 9.1 with 1N NaOH and the resulting solution was filtered.

A 1.2 mg/mL buffered protamine sulfate solution containing ethanol was prepared as described in example 1 and 0.5 mL was added to the 0.5 mL buffered $Val^8$-$Glu^{30}$-GLP-1 solution and incubated at 25° C. After 24 hours, a suspension of particles comprising $Val^8$-$Glu^{30}$-GLP-1 and protamine formed.

EXAMPLE 9

$Val^8$-$Glu^{36}$-GLP-1 Protamine Particles

A 0.5 mL buffered $Val^8$-$Glu^{36}$-GLP-1 solution was prepared by dissolving $Val^8$-$Glu^{36}$-GLP-1 in a 20 mM TRIS buffer solution to achieve a final concentration of approximately 10 mg/ml Val$^8$-Glu$^{36}$-GLP-1. The pH was adjusted to 9.2 with 1N NaOH and the resulting solution was filtered.

A 1.2 mg/mL buffered protamine sulfate solution containing ethanol was prepared as described in example 1 and 0.5 mL was added to the 0.5 mL buffered Val$^8$-Glu$^{36}$-GLP-1 solution and incubated at 25° C. After 24 hours, a suspension of particles comprising Val$^8$-Glu$^{36}$-GLP-1 and protamine formed.

EXAMPLE 10

Gly$^8$-Glu$^{22}$-GLP-1 Protamine Particles

A 0.5 mL buffered Gly$^8$-Glu$^{22}$-GLP-1 solution was prepared by dissolving Gly$^8$-Glu$^{22}$-GLP-1 in a 20 mM TRIS buffer solution to achieve a final concentration of approximately 10 mg/ml Gly$^8$-Glu$^{22}$-GLP-1. The pH was adjusted to 9.2 with 1N NaOH and the resulting solution was filtered.

A 1.2 mg/mL buffered protamine sulfate solution containing ethanol was prepared as described in example 1 and 0.5 mL was added to the 0.5 mL buffered Gly$^8$-Glu$^{22}$-GLP-1 solution and incubated at 25° C. After 24 hours, a suspension of particles comprising Gly$^8$-Glu$^{22}$-GLP-1 and protamine formed.

EXAMPLE 11

Val$^8$-Lys$^{22}$-Glu$^{30}$-GLP-1 Protamine Particles

A 0.5 mL buffered Val$^8$-Lys$^{22}$-Glu$^{30}$-GLP-1 solution was prepared by dissolving Val$^8$-Lys$^{22}$-Glu$^{30}$-GLP-1 in a 20 mM TRIS buffer solution to achieve a final concentration of approximately 10 mg/ml Val$^8$-Lys$^{22}$-Glu$^{30}$-GLP-1. The pH was adjusted to 9.5 with 1N NaOH and the resulting solution was filtered.

A 1.2 mg/mL buffered protamine sulfate solution containing ethanol was prepared as described in example 1 and 0.5 mL was added to the 0.5 mL buffered Val$^8$-Lys$^{22}$-Glu$^{30}$-GLP-1 solution and incubated at 25° C. A precipitate initially formed comprising Val$^8$-Lys$^{22}$-Glu$^{30}$-GLP-1 and protamine, but upon incubation the precipitate dissolved into solution.

EXAMPLE 12

Exendin-4 Protamine Particles

A 0.5 mL buffered Exendin-4 solution was prepared by dissolving Exendin-4 in a 20 mM TRIS buffer solution to achieve a final concentration of approximately 8 mg/ml Exendin-4. The pH was adjusted to 9.4 with 1N NaOH and the resulting solution was filtered.

A 1.2 mg/mL buffered protamine sulfate solution containing ethanol was prepared as described in example 1 and 0.5 mL was added to the 0.5 mL buffered Exendin-4 solution and incubated at 25° C. A precipitate initially formed comprising Exendin-4 and protamine, but upon incubation the precipitate dissolved into solution.

EXAMPLE 13

Protamine-Zinc Particles

An acidic zinc oxide stock solution was prepared by dissolving zinc oxide in 0.5N HCl to achieve a final concentration of 10 mg/mL. The pH of the filtered solution was between 1 and 2.

The acidic zinc oxide stock solution was added to the particle suspension of example 2 at a molar ratio of 1:1 (zinc:Val$^8$-GLP-1), and incubated at 5° C. for 18 hours. The yields as measured by UV absorbance were 100%. Polarized light microscopy revealed particles comprised of small clusters of plate-like crystals. The number mean diameter of the particles was 3.6 μm with 90% less than 9.0 μm as determined by Coulter Multisizer II (Coulter Electronics Limited, Luton, Beds, England).

EXAMPLE 14

Solubility Screening of Particles

The particle suspension of example 2 was diluted into phosphate buffered saline (PBS) such that the final concentration of Val$^8$-GLP-1 was approximately 1 mg/mL. The diluted suspension was gently stirred for one hour at room temperature. Solubility was determined by the concentration of Val$^8$-GLP-1 in the supernatant using UV absorbance measurements. The solubility of the particle suspension without zinc soaking was approximately 0.2 mg/mL.

The particle suspension of example 13 was diluted into phosphate buffered saline (PBS) such that the final concentration of Val$^8$-GLP-1 was approximately 1 mg/mL. The diluted suspension was gently stirred for one hour at room temperature. Solubility was determined by the concentration of Val$^8$-GLP-1 in the supernatant using UV absorbance measurements. The solubility of the particle suspension after zinc soaking with or without buffer was less than 0.1 mg/mL.

EXAMPLE 15

Comparison of Soluble Val$^8$-GLP-1 with Val$^8$-GLP-1 Protamine Zinc Particle Suspension A 10 mL solution of Val$^8$-GLP-1 was prepared by dissolving Val$^8$-GLP-1(7–37)OH in sterile water. Aliquots of 2N NaOH were added to aid in dissolution. The final pH of the solution was 8.5 and the Val$^8$-GLP-1(7–37)OH concentration was 0.33 mg/mL. The resulting Val$^8$-GLP-1 solution was then filtered.

The zinc soaked Val$^8$-GLP-1 protamine suspension was prepared as described in example 13 and then diluted with 20 mM TRIS such that the final concentration of Val$^8$-GLP-1 was 3.33 mg/mL.

The Val$^8$-GLP-1 protamine suspension was administered to rats via intratracheal instillation at doses of 0.5 and 5 mg/kg. The Val$^8$-GLP-1 solution was administered to rats via subcutaneous injection at a dose of 0.5 mg/kg. Blood samples were collected immediately after dosing, 10 minutes, 30 minutes, one hour and two hours after dosing to determine plasma concentration levels in pg/mL. A radioimmunoassay were used to assay plasma samples. The data are displayed in the following tables.

Plasma Concentrations of Immunoreactive Val$^8$-GLP-1 (pg/mL) in Male F344 Rats Following Subcutaneous Administration of 0.5 mg/kg Val$^8$-GLP-1 Solution.

| | Time (min) | | | | |
|---|---|---|---|---|---|
| Subject ID | 0 | 10 | 30 | 60 | 120 |
| 1001 | | 87854 | 36945 | 11348 | |
| 1002 | | 100477 | 63807 | 21434 | |

-continued

|  | Time (min) | | | | |
| --- | --- | --- | --- | --- | --- |
| Subject ID | 0 | 10 | 30 | 60 | 120 |
| 1003 |  | 175924 | 38738 | NS |  |
| 1004 |  | 111057 | 23457 | 3266 |  |
| 1005 |  |  |  |  | 1139 |
| 1006 |  |  |  |  | 1695 |
| 1007 |  |  |  |  | 1226 |
| 1008 |  |  |  |  | 3542 |
| Mean |  | 118828 | 40737 | 12016 | 1900 |
| SEM |  | 19614 | 8412 | 5255 | 561 |
| Total Number assayed |  | 4 | 4 | 3 | 4 |

NS = no sample

Plasma Concentrations of Immunoreactive $Val^8$-GLP-1 (pg/mL) in Male F344 Rats Following Intratracheal Administration of 0.5 mg/kg $Val^8$GLP-1 Protamine Particle Suspension

|  | Time (min) | | | | |
| --- | --- | --- | --- | --- | --- |
| Subject ID | 0 | 10 | 30 | 60 | 120 |
| 2001 |  | 2132 | 5173 | NR |  |
| 2002 |  | 8503 | 17458 | NR |  |
| 2003 |  | 4584 | 9764 | 9358 |  |
| 2004 |  | 5672 | 7704 | 6823 |  |
| 2005 | 510 |  |  |  | 1054 |
| 2006 | NR |  |  |  | 1351 |
| 2007 | NR |  |  |  | 1152 |
| 2008 | NR |  |  |  | 2580 |
| Mean | 510 | 5223 | 10025 | 8090 | 1534 |
| SEM | NC | 1320 | 2650 | NC | 354 |
| Total Number assayed | 1 | 4 | 4 | 2 | 4 |

NR = No Result,
NC = Not Calculated

Plasma Concentrations of Immunoreactive $Val^8$-GLP-1 (pg/mL) in Male F344 Rats Following Intratracheal Administration of 5 mg/kg $Val^8$-GLP-1 Protamine Particle Suspension

|  | Time (min) | | | | |
| --- | --- | --- | --- | --- | --- |
| Subject ID | 0 | 10 | 30 | 60 | 120 |
| 3001 |  | 40891 | 38003 | 44291 |  |
| 3002 |  | 65540 | 76197 | 32963 |  |
| 3003 |  | 33673 | 26412 | 15145 |  |
| 3004 |  | 46210 | 67193 | 44806 |  |
| 3005 | 326 |  |  |  | 51532 |
| 3006 | NR |  |  |  | NR |
| 3007 | 385 |  |  |  | 40116 |
| 3008 | 401 |  |  |  | NS |
| Mean | 371 | 46578 | 51951 | 34301 | 45824 |
| SEM | 23 | 6823 | 11786 | 6946 | NC |
| Total Number assayed | 3 | 4 | 4 | 4 | 2 |

NR = No Result,
NS = No Sample,
NC = Not Calculated

EXAMPLE 16

Comparison of $Val^8$-GLP-1 Protamine Zinc Particle Suspension with $Val^8$-GLP-1 Particle Suspension without Protamine The zinc soaked $Val^8$-GLP-1 protamine suspension was prepared as described in example 13 and then diluted with 20 mM TRIS such that the final concentration of $Val^8$-GLP-1 was 3.33 mg/mL.

A control $Val^8$-GLP-1 particle suspension was prepared without protamine.

The $Val^8$-GLP-1 protamine suspension was administered to rats via intratracheal instillation at a dose 5 mg/kg. The $Val^8$GLP-1 particle suspension without protamine was administered to rats via intratracheal instillation at a dose 5 mg/kg. Blood samples were collected after dosing, 30 minutes, two hours, and six hours after dosing to determine plasma concentration levels in pg/mL. The 5 mg/kg dose of the $Val^8$-GPL-1 protamine particle formulation resulted in measurable concentrations through 6 hours. The data are displayed in the following tables.

Plasma Concentrations of Immunoreactive $Val^8$-GLP-1 (pg/mL) in Male F344 Rats Following Intratracheal Administration of 5 mg/kg $Val^8$-GLP-1 Protamine Particle Suspension

|  | Time (hours) | | |
| --- | --- | --- | --- |
| Subject ID | 0.5 | 2 | 6 |
| 5001 | 40408 | 54505 | 36895 |
| 5002 | 51959 | 69167 | 36091 |
| 5003 | 34975 | 46204 | 22906 |
| 5004 | 29197 | 29898 | 29184 |
| Mean | 39135 | 49944 | 31269 |
| SEM | 4849 | 8196 | 3281 |
| Total Number assayed | 4 | 4 | 4 |

Plasma Concentrations of Immunoreactive $Val^8$-GLP-1 (pg/mL) in Male F344 Rats Following Intratracheal Administration of 5 mg/kg $Val^8$-GLP-1 Particle Suspension without Protamine

|  | Time (hours) | | |
| --- | --- | --- | --- |
| Subject ID | 0.5 | 2 | 6 |
| 7001 | 230108 | 23561 | 2459 |
| 7002 | 181983 | 17363 | 2433 |
| 7003 | 246594 | 17755 | 1820 |
| 7004 | 257875 | 18299 | NR |
| Mean | 229140 | 19244 | 2237 |
| SEM | 16721 | 1452 | 209 |
| N | 4 | 4 | 3 |

NR = No Result

The pharmacokinetic parameters in rats following a single 5.0 mg/kg dose of the $Val^8$-GLP-1 protamine particle suspension showed an area under the curve (AUC) of 229 (ng/mL)hr with a maximum plasma concentration reached ($C_{max}$) of 49.9 ng/mL and time to reach $C_{max}$ ($T_{max}$) of 2 hr.

EXAMPLE 17

Spray Drying $Val^8$-GLP-1 Protamine Zinc Particle Suspension $Val^8$-GLP-1 protamine particle suspensions were prepared as described in examples 13 and were spray dried using a Buchi 191 lab top spray dryer. The suspensions were spray dried using an inlet temperature of 200° C. The outlet temperature was approximately 110° C. during the drying process. The aspiration setting is about 50 mbar, nitrogen flow was 600 L/hr, and feed was about 5 mL/min. The powder was collected by a collector. The powder comprises particles with a number mean aerodynamic particle size of 2.5 μm, and 90% of the particles are less than 3.5 μm as measured using an aerosizer. The true density of the spray dried powder was 1.30 g/cc. The solubility of the powder in PBS was less than 0.1 mg/ml and had a moisture content of 7.3% as determined by Thermal Gravimetric Analysis (TGA). The peptide conformation was not changed through the spray drying process as determined by Fourier Transform InfraRed (FTIR) spectroscopy

EXAMPLE 18

Spray Drying Val$^8$-GLP-1 Protamine Zinc Particle Suspension in the Presence of DPPC A dipalmitoyl phosphatydyl choline (DPPC) stock solution was prepared by dissolving DPPC in absolute ethanol to achieve a final concentration of 5.2 mg/mL. A 100 mL solution of DPPC plus Val$^8$-GLP-1 protamine zinc particle suspension was prepared by adding 87 mLs of DPPC stock solution to 11.1 mL Val$^8$-GLP-1 protamine zinc particle suspension as described in example 13. The final concentration of DPPC was 4.5 mg/mL, the final concentration of Val$^8$-GLP-1 was 0.45 mg/mL. The resulting ratio was 10% Val$^8$-GLP-1 to 90% DPPC (w:w). The suspension was spray dried using an inlet temperature of 150° C. The outlet temperature was around 110° C. during the drying process. Scanning electron microscopy revealed two types of particles present in the spray dried powder. The powder contained flake-like particles similar to those observed in the powder prepared in example 17. However, the powder also contained more spherical shaped particles most likely composed of Val$^8$-GLP-1 protamine particles and DPPC.

EXAMPLE 19

Spray Drying Val$^8$-GLP-1 Protamine Zinc Particle Suspension in the Presence of Leucine A leucine stock solution was prepared by dissolving leucine in sterile water to achieve a final concentration of 2 mg/mL. The leucine stock solution was added to a Val$^8$-GLP-1 protamine particle suspension prepared as described in example 13 at a ratio of 3:1 to 1:3 (w/w) (Val$^8$-GLP-1: leucine). The presence of leucine in the particle suspension prior to spray drying maintained consistent powder dispersibility, but allowed the inlet temperature to be decreased from 200° C. to about 120° C. which reduced the thermal stress on the GLP-1 compound.

EXAMPLE 20

Drying by Filtration

A Val$^8$-GLP-1 protamine zinc particle suspension was prepared as described in example 13 and then filtered through a KIMAX glass filter (60 mL-40M) under mild vacuum. The collected solid was washed 4–5 times with absolute ethanol after the aqueous mother liquor passed through the filter. The solid was then left to dry at room temperature under mild vacuum. The moisture content was about 11% as determined by TGA. The powder had a number mean diameter of 2.3 μm with 90% of the particles being less than 4.7 μm as measured using an aerosizer.

EXAMPLE 21

Freeze-drying

A Val$^8$-GLP-1 protamine zinc particle suspension was prepared as described in example 13. Once particles formed the suspension was immediately frozen using a methanol dry ice bath. The frozen suspension was then dried under vacuum for 24 hours. The powder had a number mean diameter of 2.8 μm with 90% of the particles being less than 5.2 μm as measured using an aerosizer.

EXAMPLE 22

Solubility Determination of Spray Dried Powder

Val$^8$-GLP-1 protamine particle spray dried powders were prepared as described in example 17 and then resuspended in PBS and stirred gently for 1 hour. The suspensions were then centrifuged and the Val$^8$-GLP-1 concentration in the supernatants was measured by UV absorbance. The solubility of the Val$^8$-GLP-1 protamine zinc spray dried powder did not change as compared to that of the suspension prior to spray drying.

EXAMPLE 23

In Vivo Monkey Studies

A solution of Val$^8$-GLP-1 was prepared as described in example 15 and subcutaneous injections were administered to four different Cynomolgus monkeys (86131, 91071, 91811, 91901) at 100 μg/kg. A radioimmunoassay was used to assay plasma samples that were taken at various time points.

The data are displayed in the following table.

Plasma Concentrations of Immunoreactive Val$^8$-GLP-1 (ng/mL) in Cynomolgus Monkeys Following Subcutaneous Administration of 100 μg/kg of Val$^8$-GLP-1 Solution

| | Monkey numbers | | | |
|---|---|---|---|---|
| Timepoint hr) | 86131 | 91071 | 91811 | 91901 |
| 0 | BQL | BQL | BQL | BQL |
| 0.17 | 50.3 | 43.8 | 45.5 | 47.6 |
| 0.33 | 46.2 | 54.3 | 48.6 | 65.6 |
| 0.5 | 43.4 | 34.3 | 29.0 | 39.0 |
| 1 | 9.2 | 12.6 | 18.2 | 12.8 |
| 1.5 | 6.5 | 7.0 | 7.4 | 8.7 |
| 2 | 1.3 | 3.2 | 1.6 | 2.2 |
| 3 | BQL | 1.0 | BQL | 1.1 |
| 4 | BQL | BQL | BQL | BQL |
| 6 | BQL | BQL | BQL | 0.7 |
| 8 | BQL | BQL | BQL | BQL |
| 12 | BQL | BQL | BQL | BQL |
| 18 | BQL | BQL | BQL | BQL |
| 24 | BQL | 0.5 | BQL | BQL |

BQL = Below the Limit of Quantitation

Spray dried particles were prepared as described in example 17 and delivered by pulmonary administration to five different Cynomolgus monkeys (86131, 91071, 91811, 91901, 90471). The aerosol concentration was 200 μg/kg. The inhaled dose is calculated by determining the breathing volume the individual monkeys and multiplying that by the aerosization concentration. The deposited dose is estimated at 25% of the inhaled dose. Plasma samples taken at various time points were assayed by a radioimmunoassay that specifically detects immunoreactive Val$^8$-GLP-1. The data are displayed in the following table.

Plasma Concentrations of Immunoreactive Val$^8$-GLP-1 (ng/mL) in Cynomolgus Monkeys Following Pulmonary Delivery of 200 μg/kg of a Val$^8$-GLP-1 Protamine Dry Powder Formulation.

|  | Monkey numbers | | | | |
| --- | --- | --- | --- | --- | --- |
| Timepoint (hr) | 90471-P | 91811-P | 86131-P | 91071-P | 91901-P |
| 0 | 11.5 | 0.4 | BQL | BQL | 0.6 |
| 0.17 | 4.9 | 3.2 | 9.6 | 2.9 | 6.8 |
| 0.33 | 4.4 | 1.9 | 7.2 | 1.8 | 5.9 |
| 0.5 | 3.0 | 1.6 | 10.3 | 1.7 | 6.3 |
| 1 | 1.3 | 1.8 | 5.6 | 0.4 | 3.0 |
| 1.5 | 1.9 | 1.6 | 4.0 | 0.5 | 1.8 |
| 2 | 3.2 | 2.1 | 3.2 | 0.4 | 6.4 |
| 3 | 2.7 | 2.0 | 1.9 | 0.3 | 0.6 |
| 4 | 4.5 | 1.5 | 0.5 | BQL | 0.4 |
| 6 | 1.2 | 1.1 | 1.2 | BQL | BQL |
| 8 | 1.3 | 0.7 | 0.8 | BQL | BQL |
| 12 | 0.4 | BQL | BQL | 417.1 | BQL |
| 18 | 0.6 | 2.3 | BQL | BQL | BQL |
| 24 | BQL | 2.0 | BQL | BQL | BQL |
| Targeted Dose (mg/kg) | 0.200 | 0.200 | 0.200 | 0.200 | 0.200 |
| Inhaled (mg/kg) | 1.17 | 0.717 | 1.894 | 1.097 | 1.325 |
| Deposited (mg/kg) | 0.293 | 0.179 | 0.473 | 0.274 | 0.331 |

BQL = Below the Limit of Quantitation The pharmacokinetic parameters of the Cynomolgus Monkeys following dry powder aerosol exposure of 200 μg/kg of Val$^8$-GLP-1 protamineparticles and following subcutaneous administration of 100 μg/kg of Val$^8$-GLP-1 solution are shown in the following table.

| Monkey | Formulation/ Route | Dose (mg/kg) | Tmax (hr) | Cmax (ng/mL) | AUC (ng * hr/mL) | AUC/ Dose |
| --- | --- | --- | --- | --- | --- | --- |
| | Deposited | | | | | |
| 86131 | Protamine/ Pulmonary | 0.473 | 0.5 | 10.3 | 20.8 | 44.0 |
| 91071 | Protamine/ Pulmonary | 0.274 | 0.17 | 2.9 | 2.4 | 8.8 |
| 91811 | Protamine/ Pulmonary | 0.179 | 0.17 | 3.2 | 13.2 | 73.7 |
| 91901 | Protamine/ Pulmonary | 0.331 | 0.17 | 6.8 | 12.6 | 38.1 |
| 90471 | Protamine/ Pulmonary | 0.293 | 0.17 | 4.9 | 27.5 | 93.9 |
| | Injected | | | | | |
| 86131 | Solution/ Subcutaneous | 0.100 | 0.17 | 50.3 | 39.3 | 393 |
| 91071 | Solution/ Subcutaneous | 0.100 | 0.33 | 54.3 | 42.5 | 425 |
| 91811 | Solution/ Subcutaneous | 0.100 | 0.33 | 48.6 | 39.3 | 393 |
| 91901 | Solution/ Subcutaneous | 0.100 | 0.33 | 65.6 | 46.3 | 463 |

EXAMPLE 24

Dissolution of Particles

A Val$^8$-GLP-1 solution was prepared by dissolving Val$^8$GLP-1 in sterile water to achieve a final concentration of about 2 mg/mL. The pH was adjusted to 12 with 1N NaOH. After approximately 5 minutes the pH was adjusted to 7.1 with 5N HCl and the resulting solution was filtered.

A protamine sulfate solution was prepared by dissolving protamine sulfate in sterile water to achieve a final concentration of about 4 mg/mL.

One part Val$^8$-GLP-1(7–37)OH solution was combined with one part protamine solution. A precipitate formed and the pH was adjusted to 4.0. The result was a clear solution.

EXAMPLE 25

Dissolution of Particles in the Presence of Glycine

A glycine solution was prepared by dissolving glycine in sterile water to achieve a final concentration of 1M. 8 mLs of the glycine solution was combined with 4 mLs of Val$^8$-GLP-1(7–37)OH solution prepared as described in example 24 and 20 mLs of protamine solution prepared as described in example 24. The final concentration of glycine was 100 mM and the final concentration of Val$^8$-GLP-1(7–37)OH was about 1 mg/mL. The resulting pH of the mixture was 6.6. Precipitates formed immediately upon mixing. The pH was adjusted to 4.2 with 5N HCl resulting in a clear solution.

EXAMPLE 26

Spray Dried Solutions

The solutions prepared in examples 24 and 25 were spray dried using a Buchi 191 lab top spray dryer. The inlet temperature was 150° C., and the outlet temperature was around 90° C. during the drying process. The aspiration was 100%, nitrogen flow was 600 L/hr, and feed was 5.3 mL/min. Upon subsequent addition of PBS to the spray dried powder, the Val$^8$-GLP-1 protamine powder remained as a suspension, whereas a Val$^8$-GLP-1 powder prepared without protamine dissolved into solution. The spray dried powder which resulted from the solution prepared as described in example 25 comprised a Val$^8$-GLP-1 protamine glycine powder. About 14.5 mgs of this powder was resuspended in 2 mLs of PBS. The suspension was stirred gently for one hour at RT. Val$^8$-GLP-1 concentration in the supernatant was determined by UV absorbance measurements. The solubility of the Val$^8$-GLP-1 protamine glycine powder was approximately 0.3 mg/mL.

EXAMPLE 27

A solution of Val$^8$-GLP-1 is prepared as described in example 15 and subcutaneous injections were administered to three normal non-diabetic Beagle dogs. Spray dried particles are prepared as described in example 17 and delivered by pulmonary administration to the same three beagle dogs. A sham air exposure without the Val$^8$-GLP-1 molecule was used as a control. Glucose was infused at a rate of 18 mg/kg/min intravenously. The three dogs were each dosed with three different dosing regimens on three different days: a) sham air exposure without the Val$^8$-GLP-1 molecule on the first day; b) inhalation administration of the dry powder formulation of Val$^8$-GLP-1(7–37)OH at a mean inhaled dose of 1.54 mg/kg, which resulted in an estimated deposited lung dose of 362 μg/kg on a second day; and c) subcutaneous administration of the solution formulation of Val$^8$-GLP-1(7–37)OH at a dose of 200 μg/kg on a third day. Blood samples were taken periodically for the determination of plasma glucose. The results of the in vivo comparison dog study are shown in the following table.

Mean Glucose Concentrations (+SE) in Beagle Dogs Following Sham Air Exposure, Inhalation Administration of the Dry Powder Formulation of Val$^8$-GLP-1(7–37)OH, or Subcutaneous Administration of the Solution Formulation of Val$^8$-GLP-1(7–37)OH

| Time (minutes) | Sham | (SE) | Inhalation Formulation | (SE) | Subcutaneous Formulation | (SE) |
|---|---|---|---|---|---|---|
| −90 | 96 | 4 | 105 | 6 | 100 | 2 |
| −80 | 149 | 8 | 147 | 20 | 159 | 19 |
| −70 | 170 | 15 | 143 | 7 | 159 | 17 |
| −60 | 169 | 11 | 159 | 15 | 167 | 21 |
| −50 | 170 | 14 | 142 | 9 | 153 | 20 |
| −40 | 145 | 5 | 146 | 19 | 160 | 10 |
| −30 | 146 | 9 | 133 | 4 | 147 | 13 |
| −20 | 162 | 9 | 145 | 12 | 158 | 23 |
| −10 | 157 | 9 | 127 | 5 | 140 | 18 |
| 0 | 133 | 9 | 137 | 15 | 147 | 23 |
| 4 | 153 | 13 | 175 | 1 | 187 | 24 |
| 8 | 176 | 19 | 202 | 20 | 174 | 13 |

-continued

| Time (minutes) | Sham | (SE) | Inhalation Formulation | (SE) | Subcutaneous Formulation | (SE) |
|---|---|---|---|---|---|---|
| 10 | 191 | 16 | 196 | 10 | 189 | 13 |
| 20 | 213 | 25 | 207 | 16 | 192 | 13 |
| 30 | 232 | 30 | 179 | 10 | 159 | 15 |
| 40 | 253 | 53 | 165 | 1 | 152 | 13 |
| 50 | 214 | 40 | 170 | 13 | 154 | 14 |
| 60 | 206 | 28 | 160 | 7 | 165 | 17 |
| 70 | 144 | 2 | 180 | 22 | 154 | 20 |
| 80 | 135 | 2 | 162 | 12 | 152 | 19 |
| 90 | 133 | 6 | 155 | 24 | 148 | 10 |

We claim:

1. A composition comprising particles wherein the particles are comprised of a GLP-1 compound complexed with a basic polypeptide selected from the group consisting of polylysine, polyarginine, polyornithine, protamine, putrescine, spermine, spermidine, and histone, and wherein the ratio of GLP-1 compound to basic polypeptide in the composition is between about 4:1 and about 10:1 and the mean number diameter of the particles in the composition is between 1 μm and 5 μm.

2. The composition of claim 1 wherein the basic polypeptide is selected from the group consisting of polyarginine, protamine, and polylysine.

3. The composition of any claim 2 wherein the ratio of GLP-1 compound to basic polypeptide in the composition is between about 5:1 (w/w) and about 10:1 (w/w).

4. The composition of claim 3 wherein the ratio of GLP-1 compound to basic polypeptide in the composition is between about 6:1 (w/w) and about 10:1 (w/w).

5. The composition of claim 4 wherein the ratio of GLP-1 compound to basic polypeptide in the composition is between about 7:1 (w/w) and about 9:1 (w/w).

6. The composition of claim 1 wherein the particles further comprises a divalent metal ion.

7. The composition of claim 6 wherein the divalent metal ion is zinc.

8. The composition of claim 7 wherein zinc is at a molar ratio of less than about 2:1 (Zinc:GLP-1 compound).

9. The composition of claim 8 wherein zinc is at a molar ratio of about 1:6 to about 1:1 (Zinc:GLP-1 compound).

10. The composition of claim 1 wherein the particles are a dry powder.

11. The composition of claim 10 wherein the dry powder has a true density of between about 1.25 g/cc and 1.45 g/cc.

12. A method of treating a condition selected from the group consisting of diabetes, hyperglycemia, obesity, irritable bowel syndrome, myocardial infarction, and stroke comprising administering an effective amount of a composition comprising a GLP-1 compound complexed with a basic polypeptide to a patient in need thereof wherein the ratio of GLP-1 compound to basicpolypeptide in the composition is between about 4:1 and about 10:1 and the mean number diameter of the particles in the composition is between 1 μm and 5 μm.

13. The method of claim 12, wherein the composition is administered by a pulmonary route.

14. The method of claim 12, wherein the composition is delivered to a lower airway of the patient.

15. The method of claim 12, wherein the composition is inhaled through the mouth of the patient.

16. The method of claim 12, wherein the composition is delivered from an inhalation device suitable for pulmonary administration and capable of depositing the composition in the lungs of the patient.

17. The method of claim 16, wherein the device is selected from the group consisting of a nebulizer, a metered-dose inhaler, a dry powder inhaler, and a sprayer.

18. The method of claim 17, wherein the device is a dry powder inhaler.

* * * * *

```
                              SEQUENCE LISTING

<160> NUMBER OF SEQ ID NOS: 8

<210> SEQ ID NO 1
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa at 31 is Gly or is deleted.

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Ser or Gly
<220> FEATURE:
```

-continued

```
<221> NAME/KEY: MISC_FEATURE
<222> LOCATION: (3)..(3)
<223> OTHER INFORMATION: Xaa at position 3 is Asp or Glu

<400> SEQUENCE: 3

His Xaa Xaa Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is:  L-histine, D-histidine,
      or is deleted.
<220> FEATURE:
<221> NAME/KEY: MISC_FEATURE
<222> LOCATION: (2)..(2)
<223> OTHER INFORMATION: Xaa at position 2 is Ala, Gly, Ser, Thr, Leu,
      Ile, Val, Glu, Asp, or Lys
<220> FEATURE:
<221> NAME/KEY: MISC_FEATURE
<222> LOCATION: (3)..(3)
<223> OTHER INFORMATION: Xaa at position 3 is Glu, Asp, Lys, Thr, Ser,
      Arg, Trp, Phe, Tyr, or His
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, Arg, His, or Lys
<220> FEATURE:
<221> NAME/KEY: MISC_FEATURE
<222> LOCATION: (6)..(6)
<223> OTHER INFORMATION: Xaa at position 6 is His, Trp, Phe, or Tyr
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys;
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, His, Phe, or Lys
<220> FEATURE:
<221> NAME/KEY: MISC_FEATURE
<222> LOCATION: (11)..(11)
<223> OTHER INFORMATION: Xaa at position 11 is Ser, Ala, Gly Thr, Leu,
      Ile, Val, Glu, Asp, or Lys
<220> FEATURE:
<221> NAME/KEY: MISC_FEATURE
<222> LOCATION: (12)..(12)
<223> OTHER INFORMATION: Xaa at position 12 is Ser, Ala, Gly Thr, Leu,
      Ile, Val, Glu, Asp, His, Pro, Arg, or Lys
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gly, Gln, Asn, Arg, Cys, or Lys;
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, or Lys;
<220> FEATURE:
<221> NAME/KEY: MISC_FEATURE
<222> LOCATION: (15)..(15)
```

```
<223> OTHER INFORMATION: Xaa at position 15 is Glu, Asp, or Lys;
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, or Lys;
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      His, or Lys;
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, or Lys;
<220> FEATURE:
<221> NAME/KEY: MISC_FEATURE
<222> LOCATION: (20)..(20)
<223> OTHER INFORMATION: Xaa at position 20 is Lys, Arg, Gln, Glu, Asp,
      Trp, Tyr, Phe, or His;
<220> FEATURE:
<221> NAME/KEY: MISC_FEATURE
<222> LOCATION: (21)..(21)
<223> OTHER INFORMATION: Xaa at position 21 is Glu, Asp, Ala, His, Phe,
      Tyr, Trp, Arg, Leu, or Lys;
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, His, or Lys;
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      Ser, Thr, Arg, or Lys;
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys;
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, Arg, or Lys;
<220> FEATURE:
<221> NAME/KEY: MISC_FEATURE
<222> LOCATION: (28)..(28)
<223> OTHER INFORMATION: Xaa at position 28 is Lys, Arg, Glu, Asp, Asn,
      or His;
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, Arg, Trp, Tyr, Phe, Pro, His, or Lys;
<220> FEATURE:
<221> NAME/KEY: MISC_FEATURE
<222> LOCATION: (30)..(30)
<223> OTHER INFORMATION: Xaa at position 30 is Arg, Lys, Glu, Asp, Thr,
      Ser, Trp, Tyr, Phe, Gly, or His;
<220> FEATURE:
<221> NAME/KEY: MISC_FEATURE
<222> LOCATION: (31)..(31)
<223> OTHER INFORMATION: Xaa at position 31 is Gly, Ala, Ser, Thr, Leu,
      Ile, Val, Glu, Asp, His, Lys, Arg, Trp, Tyr, Phe, or is deleted;
<220> FEATURE:
<221> NAME/KEY: MISC_FEATURE
<222> LOCATION: (32)..(32)
<223> OTHER INFORMATION: Xaa at position 32 is Arg, Lys, Glu, Asp, Ser,
      or His, or is deleted;
<220> FEATURE:
<221> NAME/KEY: MISC_FEATURE
<222> LOCATION: (33)..(33)
```

```
<223> OTHER INFORMATION: Xaa at position 33 is Arg, Lys, Glu, Asp, Ser,
      or His, or is deleted;
<220> FEATURE:
<221> NAME/KEY: MISC_FEATURE
<222> LOCATION: (34)..(34)
<223> OTHER INFORMATION: Xaa at position 34 is Asp, Glu, Gly, or Lys,
      or is deleted;
<220> FEATURE:
<221> NAME/KEY: MISC_FEATURE
<222> LOCATION: (35)..(35)
<223> OTHER INFORMATION: Xaa at position 35 is Phe, Trp, Tyr, Glu, Asp,
      Ala, or Lys, or is deleted;
<220> FEATURE:
<221> NAME/KEY: MISC_FEATURE
<222> LOCATION: (36)..(36)
<223> OTHER INFORMATION: Xaa at position 36 is Pro, Lys, Glu, or Asp,
      or is deleted;
<220> FEATURE:
<221> NAME/KEY: MISC_FEATURE
<222> LOCATION: (37)..(37)
<223> OTHER INFORMATION: Xaa at position 37 is Glu, Asp, Pro, or Lys,
      or is deleted;
<220> FEATURE:
<221> NAME/KEY: MISC_FEATURE
<222> LOCATION: (38)..(38)
<223> OTHER INFORMATION: Xaa at position 38 is Glu, Asp, Pro, or Lys,
      or is deleted; and
<220> FEATURE:
<221> NAME/KEY: MISC_FEATURE
<222> LOCATION: (39)..(39)
<223> OTHER INFORMATION: Xaa at position 39 is Val, Glu, Asp, Ser, or
      Lys, or is deleted, or

<400> SEQUENCE: 4

Xaa Xaa Xaa Gly Xaa Xaa Thr Xaa Asp Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa
                20                  25                  30

Xaa Xaa Xaa Xaa Xaa Xaa Xaa
            35

<210> SEQ ID NO 5
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (5)..(5)
<223> OTHER INFORMATION: Xaa at position 5 is Asp, Glu, Arg, Thr, Ala,
      Lys, or His;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His,
      Phe, Asp, Val, Glu, or Ala;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, or Cys;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
```

```
            Gln;
<220> FEATURE:
<221> NAME/KEY: MISC_FEATURE
<222> LOCATION: (18)..(18)
<223> OTHER INFORMATION: Xaa at position 18 is Glu, His, Ala, or Lys;
<220> FEATURE:
<221> NAME/KEY: MISC_FEATURE
<222> LOCATION: (20)..(20)
<223> OTHER INFORMATION: Xaa at position 20 is Asp, Lys, Glu, or His;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: MISC_FEATURE
<222> LOCATION: (25)..(25)
<223> OTHER INFORMATION: Xaa at position 24 is Ala, Glu, Asp, Ser, or
      His;
<220> FEATURE:
<221> NAME/KEY: MISC_FEATURE
<222> LOCATION: (27)..(27)
<223> OTHER INFORMATION: Xaa at position 27 is Asp, Arg, Val, Lys, Ala,
      Gly, or Glu;
<220> FEATURE:
<221> NAME/KEY: MISC_FEATURE
<222> LOCATION: (28)..(28)
<223> OTHER INFORMATION: Xaa at position 28 is Glu, Lys, or Asp;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
<220> FEATURE:
<221> NAME/KEY: MISC_FEATURE
<222> LOCATION: (30)..(30)
<223> OTHER INFORMATION: Xaa at position 30 is Arg, Glu, or His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, Gly, or is deleted.

<400> SEQUENCE: 5

His Xaa Glu Gly Xaa Xaa Thr Ser Asp Xaa Ser Ser Tyr Leu Glu Xaa
1               5                   10                  15

Xaa Xaa Ala Xaa Xaa Phe Ile Ala Xaa Leu Xaa Xaa Xaa Xaa Xaa
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His,
      Phe, Asp, Val, Glu, or Ala;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, Cys, or Cysteic Acid;
<220> FEATURE:
<221> NAME/KEY: MISC_FEATURE
```

```
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (20)..(20)
<223> OTHER INFORMATION: Xaa at position 20 is Asp, Lys, Glu, or His;
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, - NH2, Gly, or is deleted.
<220> FEATURE:
<221> NAME/KEY: MISC_FEATURE
<222> LOCATION: (32)..(32)
<223> OTHER INFORMATION: Xaa at position 32 is Lys, Arg, Thr, Ser, Glu,
      Asp, Trp, Tyr, Phe, His, -NH2, Gly, Gly-Pro, or Gly-Pro-NH2, or
      modified residue, or is deleted.

<400> SEQUENCE: 6

His Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, Cys;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: MISC_FEATURE
<222> LOCATION: (24)..(24)
<223> OTHER INFORMATION: Xaa at position 24 is Ala Glu, Asp, Ser, or
      His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, Gly, or is deleted.

<400> SEQUENCE: 7

His Xaa Glu Gly Thr Phe Thr Ser Asp Val Ser Ser Tyr Leu Glu Xaa
1               5                   10                  15
```

-continued

```
Xaa Ala Ala Lys Xaa Phe Ile Xaa Trp Leu Val Lys Gly Arg Xaa
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      or is deleted;
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr.
<220> FEATURE:
<221> NAME/KEY: MISC_FEATURE
<222> LOCATION: (16)..(16)
<223> OTHER INFORMATION: Xaa at position 16 is Asp, Glu, Gln, Asn, Lys,
      Arg, Cys.
<220> FEATURE:
<221> NAME/KEY: MISC_FEATURE
<222> LOCATION: (31)..(31)
<223> OTHER INFORMATION: Xaa at position 31 is Gly or deleted.

<400> SEQUENCE: 8

Xaa Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Xaa
            20                  25                  30
```